US012207798B2

(12) United States Patent
Ngo Dinh et al.

(10) Patent No.: US 12,207,798 B2
(45) Date of Patent: *Jan. 28, 2025

(54) SYSTEMS AND METHODS FOR PROCESSING REAL-TIME VIDEO FROM A MEDICAL IMAGE DEVICE AND DETECTING OBJECTS IN THE VIDEO

(71) Applicant: COSMO ARTIFICIAL INTELLIGENCE—AI LIMITED, Dublin (IE)

(72) Inventors: Nhan Ngo Dinh, Rome (IT); Giulio Evangelisti, Rome (IT); Flavio Navari, Rome (IT)

(73) Assignee: COSMO ARTIFICIAL INTELLIGENCE—AI LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/525,800

(22) Filed: Nov. 30, 2023

(65) Prior Publication Data

US 2024/0108209 A1 Apr. 4, 2024

Related U.S. Application Data

(63) Continuation of application No. 18/165,232, filed on Feb. 6, 2023, now Pat. No. 11,844,499, which is a
(Continued)

(51) Int. Cl.
*G06K 9/62* (2022.01)
*A61B 1/00* (2006.01)
(Continued)

(52) U.S. Cl.
CPC .......... *A61B 1/31* (2013.01); *A61B 1/000094* (2022.02); *A61B 1/000095* (2022.02);
(Continued)

(58) Field of Classification Search
CPC . G06T 7/0012; G06T 7/10; G06T 7/11; G06T 7/70; G06T 7/73–75; G06T 7/77;
(Continued)

(56) References Cited

U.S. PATENT DOCUMENTS 6,578,017 B1 6/2003 Ebersole et al.
7,529,394 B2 5/2009 Krishnan et al.
(Continued)

FOREIGN PATENT DOCUMENTS

CN 107256552 A 10/2017
CN 107451619 A 12/2017
(Continued)

OTHER PUBLICATIONS

Ahn et al., Finding Small-Bowel Lesions: Challenges in Endoscopy-Image-Based Learning Systems, Computer, vol. 51, Issue: 5, May 2018, DOI: 10.1109/MC.2018.2381116, Date of Publication: May 24, 2018, 10 pages.
(Continued)

*Primary Examiner* — Eric Rush

(57) ABSTRACT

The present disclosure relates to systems and methods for processing real-time video and detecting objects in the video. In one implementation, a system is provided that includes an input port for receiving real-time video obtained from a medical image device, a first bus for transferring the received real-time video, and at least one processor configured to receive the real-time video from the first bus, perform object detection by applying a trained neural network on frames of the received real-time video, and overlay a border indicating a location of at least one detected object in the frames. The system also includes a second bus for receiving the video with the overlaid border, an output port for outputting the video with the overlaid border from the
(Continued)

second bus to an external display, and a third bus for directly transmitting the received real-time video to the output port.

15 Claims, 10 Drawing Sheets

Related U.S. Application Data continuation of application No. 17/379,902, filed on Jul. 19, 2021, now Pat. No. 11,574,403, which is a continuation of application No. 16/008,015, filed on Jun. 13, 2018, now Pat. No. 11,100,633.

(51) Int. Cl.

| | | |
|---|---|---|
| *A61B 1/31* | (2006.01) | |
| *A61B 5/00* | (2006.01) | |
| *G06F 18/214* | (2023.01) | |
| *G06N 3/045* | (2023.01) | |
| *G06N 3/08* | (2023.01) | |
| *G06T 7/00* | (2017.01) | |
| *G06T 7/70* | (2017.01) | |
| *G06T 11/00* | (2006.01) | |
| *G06T 11/20* | (2006.01) | |
| *G06T 11/60* | (2006.01) | |
| *G06V 10/20* | (2022.01) | |
| *G06V 10/25* | (2022.01) | |
| *G06V 10/82* | (2022.01) | |
| *G06V 20/40* | (2022.01) | |
| *G16H 30/20* | (2018.01) | |

(52) U.S. Cl.
CPC .... *A61B 1/000096* (2022.02); *A61B 1/00055* (2013.01); *A61B 5/7264* (2013.01); *A61B 5/7267* (2013.01); *G06F 18/214* (2023.01); *G06N 3/045* (2023.01); *G06N 3/08* (2013.01); *G06T 7/0012* (2013.01); *G06T 7/70* (2017.01); *G06T 11/001* (2013.01); *G06T 11/203* (2013.01); *G06T 11/60* (2013.01); *G06V 10/25* (2022.01); *G06V 10/255* (2022.01); *G06V 10/82* (2022.01); *G06V 20/40* (2022.01); *G06V 20/49* (2022.01); *G16H 30/20* (2018.01); *G06T 2207/10016* (2013.01); *G06T 2207/10068* (2013.01); *G06T 2207/20084* (2013.01); *G06T 2207/30004* (2013.01); *G06T 2207/30032* (2013.01); *G06T 2207/30064* (2013.01); *G06T 2207/30096* (2013.01); *G06V 2201/03* (2022.01); *G06V 2201/032* (2022.01)

(58) Field of Classification Search
CPC ...... G06T 11/001; G06T 11/203; G06T 11/60; G06T 2207/10016; G06T 2207/10068; G06T 2207/10072; G06T 2207/10116; G06T 2207/10132; G06T 2207/20081; G06T 2207/20084; G06T 2207/30004; G06T 2207/30024; G06T 2207/30028; G06T 2207/30032; G06T 2207/30061; G06T 2207/30064; G06T 2207/30068; G06T 2207/30096; G06V 10/25; G06V 10/255; G06V 10/70; G06V 10/82; G06V 10/98; G06V 10/987; G06V 20/40; G06V 20/49; G06V 20/69; G06V 20/695; G06V 20/698; G06V 2201/03; G06V 2201/031; G06V 2201/032; G06F 18/20; G06F 18/21; G06F 18/214; G06F 18/28; G06N 3/04; G06N 3/0427; G06N 3/045; G06N 3/0454; G06N 3/08; G06N 3/084; G06N 3/088; G16H 30/00; G16H 30/20; G16H 30/40; G16H 50/00; G16H 50/20; G16H 50/50; A61B 1/00009; A61B 1/000094; A61B 1/000095; A61B 1/000096; A61B 1/00045; A61B 1/00055; A61B 1/041; A61B 1/042; A61B 1/043; A61B 1/2736; A61B 1/31; A61B 5/72; A61B 5/7246; A61B 5/7264; A61B 5/7267; A61B 5/743
USPC ........ 382/100, 103, 128, 131–134, 155–159, 382/181, 224–227, 282, 291; 128/920, 128/922–925; 600/407, 408; 706/12, 706/14–17, 20–28, 924
See application file for complete search history.

(56) References Cited

U.S. PATENT DOCUMENTS

| | | | |
|---|---|---|---|
| 8,995,758 B1* | 3/2015 | Bissacco | G06Q 30/06 |
| | | | 382/181 |
| 9,530,205 B2 | 12/2016 | Kim et al. | |
| 10,037,471 B2 | 7/2018 | Satzoda et al. | |
| 10,242,292 B2 | 3/2019 | Zisimopoulos et al. | |
| 10,460,256 B2 | 10/2019 | Amershi et al. | |
| 10,475,174 B2* | 11/2019 | Lim | G06V 10/82 |
| 10,504,004 B2 | 12/2019 | Kaufhold et al. | |
| 10,540,578 B2* | 1/2020 | Madani | G06V 10/774 |
| 10,592,779 B2 | 3/2020 | Madani et al. | |
| 10,706,534 B2 | 7/2020 | Middlebrooks et al. | |
| 10,799,098 B2 | 10/2020 | Oosake | |
| 10,810,460 B2 | 10/2020 | Dinh et al. | |
| 10,841,514 B2 | 11/2020 | Sachdev et al. | |
| 10,892,050 B2 | 1/2021 | Zhang et al. | |
| 11,033,251 B2 | 6/2021 | Srinivasan et al. | |
| 11,049,243 B2 | 6/2021 | Odry et al. | |
| 11,132,792 B2 | 9/2021 | Zhang et al. | |
| 11,132,795 B2 | 9/2021 | Endo | |
| 11,210,777 B2 | 12/2021 | Fitzgerald et al. | |
| 11,844,499 B2 | 12/2023 | Dinh et al. | |
| 2006/0045312 A1 | 3/2006 | Bernstein et al. | |
| 2006/0133699 A1 | 6/2006 | Widrow et al. | |
| 2008/0058593 A1 | 3/2008 | Gu et al. | |
| 2008/0159622 A1 | 7/2008 | Agnihotri et al. | |
| 2009/0034810 A1 | 2/2009 | Oakley | |
| 2010/0303322 A1 | 12/2010 | Whelan et al. | |
| 2011/0301447 A1 | 12/2011 | Park et al. | |
| 2012/0304008 A1 | 11/2012 | Hackstein et al. | |
| 2014/0193051 A1 | 7/2014 | Lee et al. | |
| 2014/0301619 A1 | 10/2014 | Stavros et al. | |
| 2015/0117729 A1 | 4/2015 | Kim et al. | |
| 2016/0078625 A1 | 3/2016 | Tajbakhsh et al. | |
| 2017/0132468 A1 | 5/2017 | Mosher et al. | |
| 2017/0172458 A1 | 6/2017 | Kato et al. | |
| 2017/0265747 A1 | 9/2017 | Tajbakhsh et al. | |
| 2017/0286805 A1 | 10/2017 | Yu et al. | |
| 2017/0300814 A1 | 10/2017 | Shaked et al. | |
| 2017/0316286 A1 | 11/2017 | Szegedy et al. | |
| 2018/0012463 A1 | 1/2018 | Chaudhry et al. | |
| 2018/0075599 A1 | 3/2018 | Tajbakhsh et al. | |
| 2018/0225820 A1 | 8/2018 | Liang et al. | |
| 2018/0247107 A1 | 8/2018 | Murthy et al. | |
| 2018/0253839 A1 | 9/2018 | Zur | |
| 2018/0341833 A1 | 11/2018 | Bernard et al. | |
| 2018/0357514 A1 | 12/2018 | Zisimopoulos et al. | |
| 2018/0360431 A1 | 12/2018 | Threlfall et al. | |
| 2018/0365826 A1 | 12/2018 | Oh et al. | |
| 2019/0080205 A1 | 3/2019 | Kaufhold et al. | |
| 2019/0080454 A1 | 3/2019 | Hameed et al. | |
| 2019/0156202 A1 | 5/2019 | Falk et al. | |
| 2019/0197358 A1 | 6/2019 | Madani et al. | |
| 2019/0231444 A1 | 8/2019 | Tojo et al. | |
| 2019/0252073 A1 | 8/2019 | Hsu et al. | |
| 2019/0297276 A1 | 9/2019 | Sachdev et al. | |
| 2019/0304092 A1 | 10/2019 | Akselrod-Ballin et al. | |
| 2019/0311476 A1 | 10/2019 | Hayami et al. | |
| 2019/0311478 A1 | 10/2019 | Avendi et al. | |
| 2019/0325621 A1 | 10/2019 | Wang et al. | |

(56) References Cited

U.S. PATENT DOCUMENTS

| | | | |
|---|---|---|---|
| 2019/0380617 | A1 | 12/2019 | Oosake et al. |
| 2019/0385018 | A1 | 12/2019 | Dinh et al. |
| 2019/0385302 | A1 | 12/2019 | Dinh et al. |
| 2020/0008653 | A1 | 1/2020 | Kamon |
| 2020/0069160 | A1 | 3/2020 | Oosake |
| 2020/0226423 | A1 | 7/2020 | Dinh et al. |
| 2020/0337537 | A1 | 10/2020 | Hirasawa et al. |
| 2021/0018742 | A1 | 1/2021 | Stumpe |
| 2021/0022586 | A1 | 1/2021 | Mori et al. |
| 2021/0133507 | A1 | 5/2021 | Dinh et al. |
| 2021/0133972 | A1 | 5/2021 | Dinh et al. |
| 2021/0153730 | A1 | 5/2021 | Karino |
| 2021/0153808 | A1 | 5/2021 | Tada et al. |

FOREIGN PATENT DOCUMENTS

| | | |
|---|---|---|
| CN | 107451994 A | 12/2017 |
| WO | 2016161115 A1 | 10/2016 |
| WO | 2017042812 A2 | 3/2017 |

OTHER PUBLICATIONS

Moeskops et al., Adversarial training and dilated convolutions for brain MRI segmentation, Conference: International Workshop on Deep Learning in Medical Image Analysis International Workshop on Multimodal Learning for Clinical Decision Support, Lecture Notes in Computer Science, DOI: 10.1007/978-3-319-67558-9_7, First Online: Sep. 2017, dated Jul. 11, 2017, 8 pages.

Ross et al., Exploiting the potential of unlabeled endoscopic video data with self-supervised learning, International Journal of Computer Assisted Radiology and Surgery 13(9), DOI: 10.1007/s11548-018-1772-0, dated Nov. 27, 2017, 13 pages.

Schlegl et al., Unsupervised Anomaly Detection with Generative Adversarial Networks to Guide Marker Discovery, Information Processing in Medical Imaging, Lecture Notes in Computer Science, vol. 10265, Published May 23, 2017, 12 pages.

Billah et al., "An Automatic Gastrointestinal Polyp Detection System in Video Endoscopy Using Fusion of Color Wavelet and Convolutional Neural Network Features," International Journal of Biomedical w Imaging, vol. 2017, published Aug. 14, 2017, 10 pages.

Byrne et al., "Artificial Intelligence (AI) in Endoscopy-Deep Learning for Optical Biopsy of Colorectal Polyps in Real-Time on Unaltered Endoscopic Videos," Gastrointestinal Endoscopy Supplement, vol. 85, No. 5, May 2017, pp. AB364-AB365.

Byrne et al., "Real-time differentiation of adenomatous and hyperplastic diminutive colorectal polyps during analysis of unaltered videos of standard colonoscopy using a deep learning model," Gut, published Oct. 24, 2017, 7 pages.

Byrne et al., "Will Computer-Aided Detection and Diagnosis Revolutionize Colonoscopy?" Gastroenterology, vol. 152, No. 6, published Oct. 31, 2017, pp. 1460-1464.e1.

Chen et al., "Accurate Classification of Diminutive Colorectal Polyps Using Computer-Aided Analysis," Gastroenterology, vol. 154, No. 3, Feb. 2018, pp. 568-574.

Feichtenhofer et al., "Detect to Track and Track to Detect," Proceedings of the IEEE International Conference on Computer Vision (ICCV), published Oct. 22, 2017, pp. 3038-3046.

Frid-Adar et al., "Gan-based Synthetic Medical Image Augmentation for Increased CNN Performance in Liver Lesion Classification," arXiv:1803.01229v1, submitted on Mar. 3, 2018, 10 pages.

Hadjilucas "Framework for the Detection and Classification of Colorectal Polyps," PhD dissertation, Imperial College of Science, Technology and Medicine, London, United Kingdom, Date Awarded: Jul. 2014, 142 pages.

Henriksen et al., Polyp Detection using Neural Networks-Data Enhancement and Training Optimization, Master's Thesis, Department of Informatics, University of Oslo, Oslo, Norway, May 2017, 115 pages.

International Search Report, International Application No. PCT/EP2019/065258 for Cosmo Artificial Intelligence—AL Limited, mailed Aug. 20, 2019, 2 pages.

Kang et al., "Object Detection from Video Tubelets with Convolutional Neural Networks," 2016 IEEE Conference on Computer Vision and Pattern Recognition, Date of Conference: Jun. 27-30, 2016, Las Vegas, NV, USA, pp. 817-825.

Karnes et al., "Automated Polyp Detection Using Deep Learning: Leveling the Field," Gastrointestinal Endoscopy, vol. 85, No. 5, May 2017, pp. AB376-AB377.

Li et al., "Perceptual Generative Adversarial Networks for Small Object Detection," Proceedings of the IEEE Conference on Computer Vision and Pattern Recognition (CVPR), Jun. 2017, pp. 1222-1230.

Liu "Deep Learning Applied to Automatic Polyp Detection in Colonoscopy Images," Master's Thesis, University College of Southeast Norway, Kongsberg, Norway, 2017, 105 pages.

Maghsoudi "Superpixels Based Segmentation and SVM Based Classification Method to Distinguish Five Diseases from Normal Regions in Wireless Capsule Endoscopy," Department of Bioengineering, College of Engineering, Temple University, Philadelphia, PA, USA, published Nov. 2017, 13 pages.

Mahmood et al., "Deep Learning and Conditional Random Fields-based Depth Estimation and Topographical Reconstruction from Conventional Endoscopy," Medical Image Analysis, vol. 48, Aug. 2018, pp. 230-243.

Mori et al., "Computer-aided diagnosis for colonoscopy," Endoscopy, vol. 49, No. 8, Aug. 2017, pp. 813-819.

Oliva et al., "Prototype system for feature extraction, classification and study of medical images," Expert Systems with Applications, vol. 63, Nov. 2016, pp. 267-283.

Pogorelov et al., "Efficient disease detection in gastrointestinal videos—global features versus neural networks," Multimedia Tools Applications, vol. 76, published online Jul. 19, 2017, pp. 22493-22525.

Ribeiro et al., "Transfer Learning for Colonic Polyp Classification Using Off-the-Shelf CNN Features," In Computer-Assisted and Robotic Endoscopy: Third International Workshop, CARE 2016, Held in Conjunction with MICCAI 2016, Athens, Greece, Oct. 17, 2016, Revised Selected Papers 3, Springer International Publishing, pp. 1-13.

Riegler "EIR—A Medical Multimedia System for Efficient Computer Aided Diagnosis," PhD Thesis, University of Oslo, Oslo, Norway, 2017, 281 pages.

Schlegal et al., "Unsupervised Anomaly Detection with Generative Adversarial Networks to Guide Marker Discovery", Information Processing in Medical Imaging, Lecture Notes in Computer Science, vol. 10265, Published May 23, 2017, pp. 146-157.

Search Report in European Application No. 18180572.2 dated Feb. 20, 2019, 8 pages.

Tajbakhsh et al., "Automated Polyp Detection in Colonoscopy Videos Using Shape and Context Information," IEEE Transactions on Medical Imaging, vol. 32, No. 2, Feb. 2016, pp. 630-644.

Tajbakhsh et al., "Convolutional Neural Networks for Medical Image Analysis: Fine Tuning or Full Training?" IEEE Transactions on Medical Imaging, vol. 35, No. 5, May 2016, pp. 1299-1312.

Tamaki et al., "Computer-aided colorectal tumor classification in NBI endoscopy using local features," Medical Image Analysis, vol. 17, No. 1, Jan. 2013, pp. 78-100.

Vázquez et al., "A Benchmark for Endoluminal Scene Segmentation of Colonoscopy Images," Journal of Healthcare Engineering, vol. 2017, published Jul. 26, 2017, 9 pages.

Wang et al., "Polyp-Alert: Near real-time feedback during colonoscopy," Computer Methods and Programs in Biomedicine, vol. 120, No. 3, Jul. 2015, pp. 164-179.

Wimmer et al., "Directional wavelet based features for colonic polyp classification," Medical Image Analysis, vol. 31, Jul. 2016, pp. 16-36.

Yu et al., "Integrating Online and Offline Three-Dimensional Deep Learning for Automated Polyp Detection in Colonoscopy Videos," IEEE Journal of Biomedical and Health Informatics, vol. 21, No. 1, Jan. 2017, pp. 65-75.

(56) References Cited

OTHER PUBLICATIONS

Yuan et al., "Automatic Polyp Detection in Colonoscopy Videos," Medical Imaging 2017: Image Processing, Feb. 24, 2017, 10 pages.

Yuan et al., "Deep learning for polyp recognition in wireless capsule endoscopy images," Medical Physics, vol. 44, No. 4, Apr. 2017, pp. 1379-1289.

Yuan et al., "Improved Bag of Feature for Automatic Polyp Detection in Wireless Capsule Endoscopy Images," IEEE Transactions on Automation Science and Engineering, vol. 13, No. 2, Apr. 2016, pp. 529-535.

Zhang et al., "Automatic Detection and Classification of Colorectal Polyps by Transferring Low-level CNN Features from Nonmedical Domain," IEEE Journal of Biomedical and Health Informatics, vol. 21, No. 1, Jan. 2017, pp. 41-47.

Zhu et al. "Deep Feature Flow for Video Recognition," Proceedings of the IEEE conference on computer vision and pattern recognition, submitted on Nov. 23, 2017, pp. 2349-2358.

International Search Report, International Application No. PCT/EP2019/065256 for Cosmo Artificial Intelligence—AL Limited, mailed Sep. 17, 2019 (5 pages).

Patrick Brandao et al., "Towards a Computed-Aided Diagnosis System in Colonoscopy: Automatic Polyp Segmentation Using Convolution Neural Networks," Journal of Medical Robotics Research, vol. 03, No. 02, Feb. 23, 2018, pp. 1840002-1 to 1840002-13 (10 pages).

Search Report in European Application No. 18180570.6 dated Feb. 12, 2019 (8 pages).

* cited by examiner

SYSTEMS AND METHODS FOR PROCESSING REAL-TIME VIDEO FROM A MEDICAL IMAGE DEVICE AND DETECTING OBJECTS IN THE VIDEO

CROSS-REFERENCE TO RELATED APPLICATIONS

This application is a continuation application of and claims priority for patent entitled to a filing date and claiming the benefit of earlier-filed U.S. Pat. No. 11,844,499, issued Dec. 19, 2023, which is a continuation application of and claims priority to U.S. Pat. No. 11,574,403, issued Feb. 7, 2023, which is a continuation application of and claims priority to U.S. Pat. No. 11,100,633, issued Aug. 24, 2021. Each patent application cited herein is hereby incorporated by reference in its entirety.

TECHNICAL FIELD

The present disclosure relates generally to the field of neural networks and the use of such networks for image analysis and object detection. More specifically, and without limitation, this disclosure relates to computer-processing systems and methods for training generative adversarial networks and processing real-time video. The systems and methods and trained neural networks disclosed herein may be used in various applications and vision systems, such as medical image analysis and systems that benefit from accurate object detection capabilities.

BACKGROUND

In many object detection systems, an object is detected in an image. An object of interest may be a person, place, or thing. In some applications, such as medical image analysis and diagnosis, the location of the object is important as well. However, computer-implemented systems that utilize image classifiers are typically unable to identify or provide the location of a detected object. Accordingly, extant systems that only use image classifiers are not very useful.

Furthermore, training techniques for object detection may rely on manually annotated training sets. Such annotations are time-consuming when the detection network being trained is one that is bounding box-based, such as a You Only Look Once (YOLO) architecture, a Single Shot Detector (SSD) architecture, or the like. Accordingly, large datasets are difficult to annotate tor training, often resulting in a neural network that is trained on a smaller dataset, which decreases accuracy.

For computer-implemented systems, extant medical imaging is usually built on a single detector network. Accordingly, once a detection is made, the network simply outputs the detection, e.g., to a physician or other health care professional. However, such detections may be false positives, such as non-polyps in endoscopy or the like. Such systems do not provide a separate network for differentiating false positives from true positives.

Furthermore, object detectors based on neural networks usually feed features identified by a neural network into the detector, which may comprise a second neural network. However, such networks are often inaccurate because feature detection is performed by a generalized network, with only the detector portion being specialized.

Finally, many extant object detectors function on a delay. For example, medical images may be captured and stored before analysis. However, some medical procedures, such as endoscopy, are diagnosed on a real-time basis. Consequently, these systems are usually difficult to apply in the required real-time fashion.

SUMMARY

In view of the foregoing, embodiments of the present disclosure provide computer-implemented systems and methods for training a generative adversarial network and using the same for applications such as medical image analysis. The systems and methods of the present disclosure provide benefits over extant system and techniques, including improved object detection and location information.

In accordance with some embodiments, a computer-implemented system is provided that includes an object detector network that identifies features-of-interest (i.e., abnormalities or objects of interest), along with locations thereof, and an adversarial network that distinguishes true positives from false positives. Moreover, embodiments of the present disclosure provide a two-loop technique for training the object detector network. This training process uses annotations based on reviewing a detection, such that manual annotation may occur much faster and therefore with a larger dataset. Moreover, this process may be used to train a generative adversarial network to distinguish false positives from true positives.

In addition, disclosed systems are provided that combine an object detector network with a generative adversary network. By combining such networks, false positives may be distinguished from true positives, thereby providing more accurate outputs. By reducing false positives, a physician or other health care professional may give increased attention to outputs from the network on account of the increased accuracy.

Furthermore, embodiments of the present disclosure include neural networks that do not use generic feature identification by one neural network combined with a specialized detector. Rather, a single, seamless neural network is trained for the object detector portion, which results in greater specialization, as well as increased accuracy and efficiency.

Finally, embodiments of the present disclosure are configured for displaying real-time video (such as endoscopy video or other medical images) along with object detections on a single display. Accordingly, embodiments of the present disclosure provide a video bypass to minimize potential problems from errors and other potential drawbacks with the object detector. Moreover, the object detections may be displayed in particularized ways designed to better draw the attention of the physician or other health care professional.

In one embodiment, a system for processing real-time video may comprise an input port for receiving real-time video; a first bus for transferring the received real-time video; at least one processor configured to receive the real-time video from the first bus, perform object detection on frames of the received real-time video, and overlay a border indicating a location of at least one detected object in the frames; a second bus for receiving the video with the overlaid border; an output port for outputting the video with the overlaid border from the second bus to an external display; and a third bus for directly transmitting the received real-time video to the output port.

In one embodiment, a system tor processing real-time video may comprise an input port for receiving real-time video; at least one processor configured to receive the real-time video from the input port, perform object detection by applying a trained neural network on frames of the received real-time video, and overlay a border indicating a location of at least one detected object in the frames; an output port for outputting the video with the overlaid border from the at least one processor to an external display; and an input device tor receiving a sensitivity setting from a user. The processor may be further configured to adjust at least one parameter of the trained neural network in response to the sensitivity setting.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the disclosed embodiments.

BRIEF DESCRIPTION OF THE DRAWINGS

The accompanying drawings, which comprise a part of this specification, illustrate several embodiments and, together with the description, serve to explain the principles and features of the disclosed embodiments. In the drawings.

DETAILED DESCRIPTION

The disclosed embodiments relate to computer-implemented systems and methods for training generative adversarial networks and using the same. Advantageously, the exemplary embodiments can provide improved trained networks and fast and efficient object detection. Embodiments of the present disclosure can also provide improved object detection for medical image analysis, with reduced false positives.

Embodiments of the present disclosure may be implemented and used in various applications and vision systems. For example, embodiments of the present disclosure may be implemented for medical image analysis systems and other types of systems that benefit from object detection where the objects may be true or false positives. Although embodiments of the present disclosure are described herein with general reference to medical image analysis and endoscopy, it will be appreciated that the embodiments may be applied to other medical image procedures, such as gastroscopy, colonoscopy, and enteroscopy. Further, embodiments of the present disclosure are not limited to other environments and vision systems, such as those for or including LIDAR, surveillance, auto-piloting, and other imaging systems.

Figure 1:
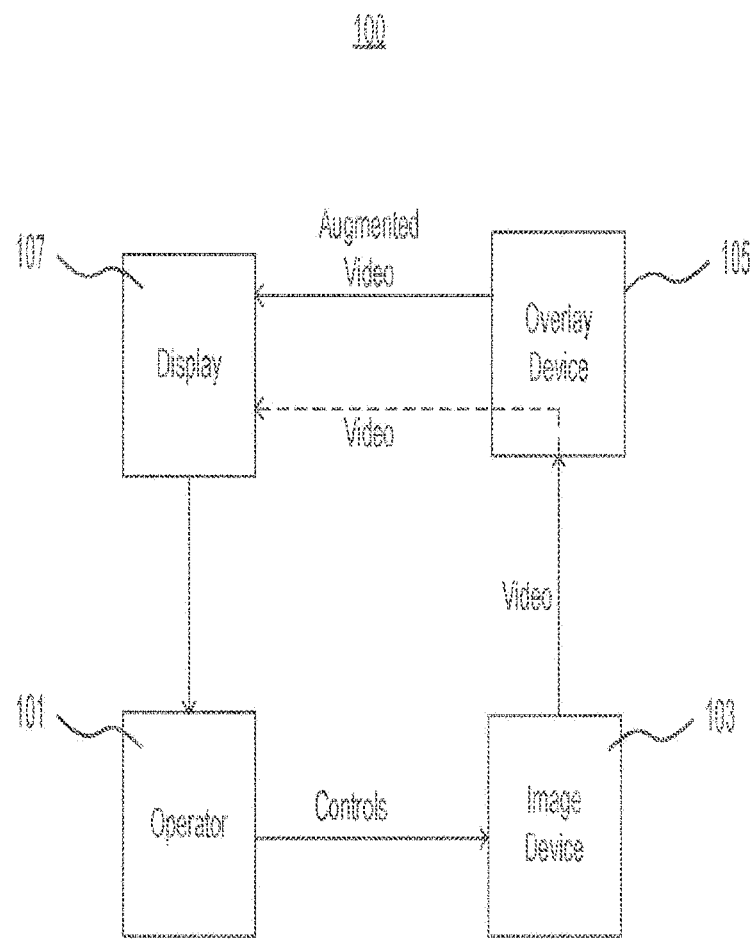
FIG. 1 is a schematic representation of an exemplary computer-implemented system for overlaying object detections on a video feed, according to embodiments of the present disclosure.
Figure 6:
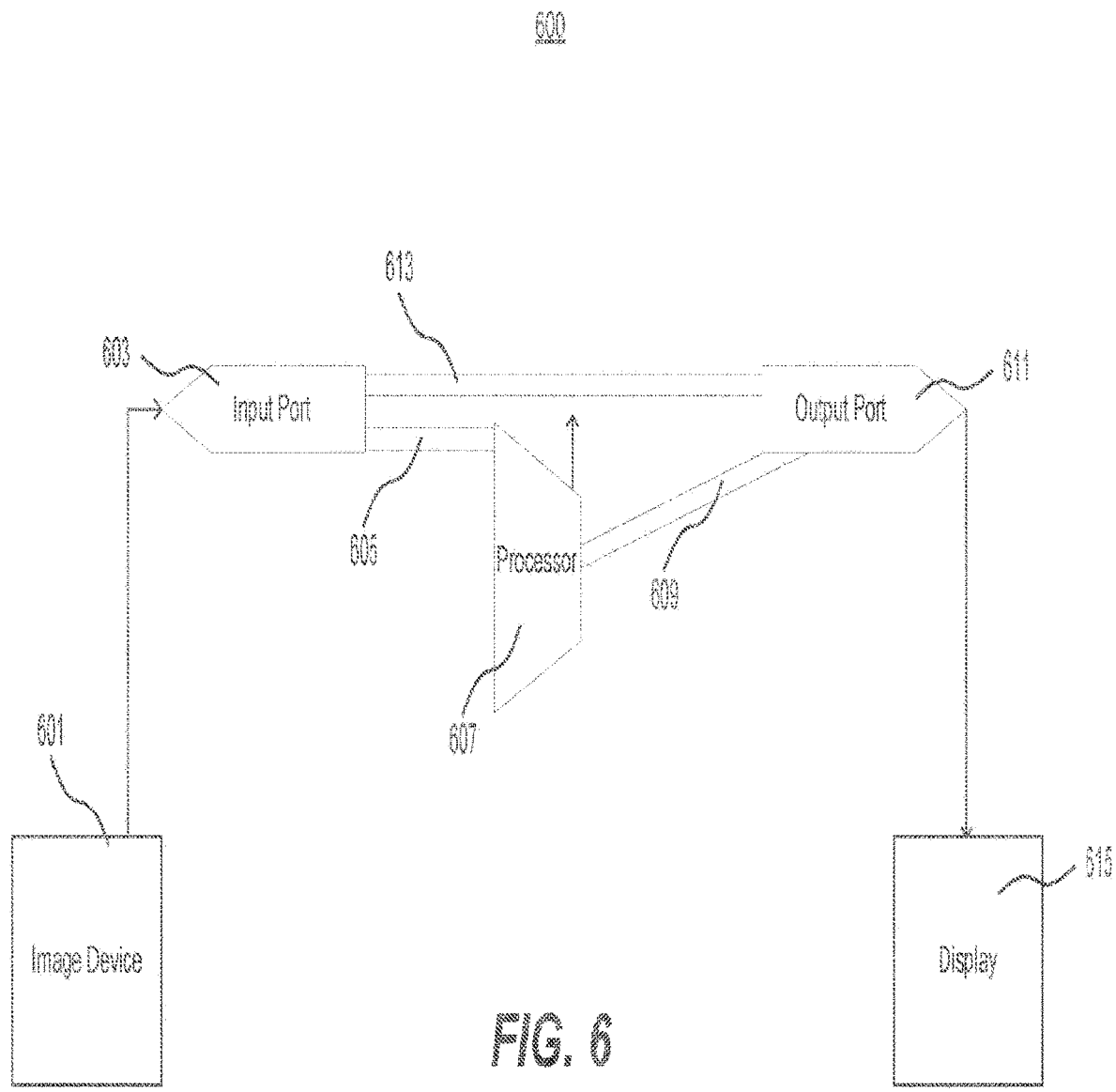
FIG. 6 is a schematic representation of a computer-implemented system using an object detector network, according to embodiments of the present disclosure.

According to an aspect of the present disclosure, a computer-implemented system is provided for training a generative adversarial network using images including representations of a feature-of-interest The system may include at least one memory configured to store instructions and at least one processor configured to execute the instructions (see, e.g., FIGS. 1 and 6). The at least one processor may provide a first plurality of images. For example, the at least one processor may extract the first plurality of images from one or more databases. Additionally or alternatively, the first plurality of images may comprise a plurality of frames extracted from one or more videos.

As used herein, the term "image" refers to any digital representation of a scene or field of view. The digital representation may be encoded in any appropriate format, such as Joint Photographic Experts Group (JPEG) format, Graphics interchange Format (GIF), bitmap format, Scalable Vector Graphics (SVG) format, Encapsulated Postscript (EPS) format, or the like. Similarly, the term "video" refers to any digital representation of a scene or area of interest comprised of a plurality of images in sequence. The digital representation may be encoded in any appropriate format, such as a Moving Picture Experts Group (MPEG) format, a flash video format, an Audio Video Interleave (AVI) format, or the like. In some embodiments, the sequence of images may be paired with audio.

The first plurality of images may include representations of the feature-of-interest (i.e., an abnormality or object of interest) and indicators of the locations of the feature-of-interest in images of the first plurality of images. For example, the feature-of-interest may comprise an abnormality on or of human tissue. In some embodiments, the feature-of-interest may comprise an object, such as a vehicle, person, or other entity.

In accordance with the present disclosure, an "abnormality" may include a formation on or of human tissue, a change in human tissue from one type of cell to another type of cell, and/or an absence of human tissue from a location where the human tissue is expected. For example, a tumor or other tissue growth may comprise an abnormality because more cells are present than expected. Similarly, a bruise or other change in cell type may comprise an abnormality because blood cells are present in locations outside of expected locations (that is, outside the capillaries). Similarly, a depression in human tissue may comprise an abnormality because cells are not present in an expected location, resulting in the depression.

In some embodiments, an abnormality may comprise a lesion. Lesions may comprise lesions of the gastro-intestinal mucosa. Lesions may be histologically classified (e.g., per the Vienna classification), morphologically classified (e.g., per the Paris classification), and/or structurally classified (e.g., as serrated or not serrated). The Paris classification includes polyploid and non-polyploid lesions. Polyploid lesions may comprise protruded, pedunculated and protruded, or sessile lesions. Non-polyploid lesions may comprise superficial elevated, flat, superficial shallow depressed, or excavated lesions.

In regards to detected abnormalities, serrated lesions may comprise sessile serrated adenomas (SSA); traditional serrated adenomas (TSA); hyperplastic polyps (HP); fibroblastic polyps (FP); or mixed polyps (MP). According to the Vienna classification, an abnormality is divided into five categories, as follows: (Category 1) negative for neoplasia/dysplasia; (Category 2) indefinite for neoplasia/dysplasia; (Category 3) non-invasive low grade neoplasia (low grade adenoma/dysplasia); (Category 4) mucosal high grade neoplasia, such as high grade adenoma/dysplasia, non-invasive carcinoma (carcinoma in-situ), or suspicion of invasive carcinoma; and (Category 5) invasive neoplasia, intramucosal carcinoma, submucosal carcinoma, or the like.

The indicators of the locations of an abnormality or feature-of-interest may comprise points (e.g., coordinates) or regions (e.g., a rectangle, a square, an oval, or any other regular or irregular shape). The indicators may comprise manual annotations on or of the images. In some embodiments, the first plurality of images may comprise medical images, such as images of a gastro-intestinal organ or other organ or area of human tissue. The images may be generated from a medical imaging device, such as those used during an endoscopy, a gastroscopy, a colonoscopy, or an enteroscopy procedure. In such embodiments, if the feature-of-interest is a lesion or other abnormality, a physician or other health care professional may annotate the images to place indicators of the abnormality in the images.

The processor(s) of the system may use the first plurality of images and indicators of the feature-of-interest to train an object detection network to detect the feature-of-interest. For example, the object detection network may comprise a neural network with one of more layers configured to accept an image as input and to output an indicator of a location of a feature-of-interest In some embodiments, the object detection network may comprise a convolutional network.

Training the object detection network may include adjusting weights of one or more nodes of the network and/or adjusting activation (or transfer) functions of one or more nodes of the network. For example, weights of the object detection network may be adjusted to minimize a loss function associated with the network. In some embodiments, the loss function may comprise a square loss function, a hinge loss function, a logistic loss function, a cross entropy loss function, or any other appropriate loss function or combination of loss functions. In some embodiments, activation (or transfer) functions of the object detection network may be modified to improve the fit between one or more models of the node(s) and the input to the node(s). For example, the processor(s) may increase or decrease the power of a polynomial function associated with the node(s), may change the associated function from one type to another (e.g., from a polynomial to an exponential function, from a logarithmic functions to a polynomial, or the like), or perform any other adjustment to the model(s) of the node(s).

The system processor(s) may further provide a second plurality of images that include representations of the feature-of-interest. For example, the processor(s) may extract the first plurality of images from one or more databases, whether the same database(s) that stored the first plurality of images or one or more different databases. Additionally or alternatively, the second plurality of images may comprise a plurality of frames extracted from one or more videos, whether the same video(s) used to extract the first plurality of images or one or more different videos.

In some embodiments, the second plurality of images may comprise medical images, such as images from an endoscopy device. In such embodiments, the feature-of-interest may comprise a lesion or other abnormality.

In some embodiments, the second plurality of images may comprise a larger number of images than that included in the first plurality of images. For example, the second plurality of images may include at least one hundred times more images than the first plurality of images. In some embodiments, the second plurality of images may include the first plurality, at least in part, or may be different images from the first plurality. In embodiments where the second plurality of images are extracted, at least in part, from one or more videos from which at least part of the first plurality of images were extracted, the second plurality of images may comprise different frames than the first plurality from the same video(s).

The system processor(s) may apply the trained object detection network to the second plurality of images to produce a first plurality of detections of the feature-of-interest. For example, in embodiments where the trained object detection network comprises a neural network, the at least one processor may input the second plurality of images to the network and receive the detections. The detections may comprise indicators of locations of the feature-of-interest in the second plurality of images. If the second plurality of images does not include the feature-of-interest, the indicator may comprise a null indicator or other indicator of no feature-of-interest.

The system processor(s) may further provide manually set verifications of true positives and false positives with respect to the first plurality of detections. For example, the verifications may be extracted from one or more databases or received as input. In embodiments where the feature-of-interest comprises a lesion or other abnormality, the verifications may be entered by a physician or other health care professional. For example, the processor(s) may output the detections for display to the physician or other health care professional and receive the verifications in response to the displayed detections.

The system processor(s) may use the verifications of the true positives and false positives with respect to the first plurality of detections to train a generative adversarial network. For example, a generative branch of the network may be trained to generate artificial representations of the feature-of-interest. Accordingly, the generative branch may comprise a convolutional neural network.

Similar to the object detection network, training the generative branch may include adjusting weights of one or more nodes of the network and/or adjusting activation (or transfer) functions of one or more nodes of the network. For example, as explained above, weights of the generative branch may be adjusted to minimize a loss function associated with the network. Additionally or alternatively, activation (or transfer) functions of the generative branch may be modified to improve the fit between one or more models of the node(s) and the input to the node(s).

Moreover, the adversarial branch of the network may be trained to distinguish false positives from true positives based on the manual verifications. For example, the adversarial branch may comprise a neural network accepting an image and one or more corresponding detection as input and producing a verification as output. In some embodiments, the processor(s) may further retrain the generative network by providing verifications of false negatives for missed detections of the feature-of-interest in two or more images. By providing artificial representations from the generative branch as input to the adversarial branch and recursively using output from the adversarial branch, the adversarial branch and generative branch may perform unsupervised learning.

Similar to the generative branch, training the adversarial branch may include adjusting weights of one or more nodes of the network and/or adjusting activation (or transfer) functions of one or more nodes of the network. For example, as explained above, weights of the adversarial branch may be adjusted to minimize a loss function associated with the network. Additionally or alternatively, activation (or transfer) functions of the adversarial branch may be modified to improve the fit between one or more models of the node(s) and the input to the node(s).

Accordingly, in embodiments where the feature-of-interest comprises a lesion or other abnormality, the generative branch may be trained to generate representations of non-abnormalities that look similar to abnormalities, and the adversarial branch may be trained to distinguish artificial non-abnormalities from abnormalities in the second plurality of images.

The system processor(s) may retrain the generative adversarial network using at least one further set of images and detections of the feature-of-interest, together with further manually set verifications of true positives and false positives with respect to the further detections of the feature-of-interest. For example, the processor(s) may extract the further set of images from one or more databases, whether the same database(s) that stored the first plurality of images and/or the second plurality of images or one or more different databases. Additionally or alternatively, the further set of images may comprise a plurality of frames extracted from one or more videos, whether the same video(s) used to extract the first plurality of images and/or the second plurality of images or one or more different videos. Similar to training, retraining the adversarial branch may include further adjustments to the weights of one or more nodes of the network and/or further adjustments to the activation (or transfer) functions of one or more nodes of the network.

According to another aspect of the present disclosure, a computer-implemented method is provided for training a neural network system to detect abnormalities in images of a human organ. The method may be implemented by at least one processor (see, e.g., processor 607 of FIG. 6).

According to the exemplary method, the processor(s) may store, in a database, a plurality of videos including representations of abnormalities. For example, the videos may comprise endoscopy videos. The videos may be encoded in one or more formats, such as a Moving Picture Experts Group (MPEG) format, a flash video format, an Audio Video Interleave (AVI) format, or the like.

The method may further include selecting, with the processor(s), a first subset of the plurality of videos. For example, the processor(s) may randomly select the first subset. Alternatively, the processor(s) may use one or more indices of the database to select the first subset. For example, the processor(s) may select the first subset as videos indexed as including representations of abnormalities.

The method may further include applying, with the processor(s), a perception branch of an object detection network to frames of the first subset of the plurality of videos to produce a first plurality of detections of abnormalities. For example, the object detection network may comprise a neural network trained to accept images as input and to output the first plurality of detections. The first plurality of detections may comprise indicators of locations of abnormalities in the frames, such as a point or a region of a detected abnormality. A lack of an abnormality may result in a null indicator or other indicator of no abnormality. The perception branch may comprise a neural network (e.g., a convolutional neural network) configured to detect polyps and output indicators of locations of any detected abnormalities.

The method may further include selecting, with the processor(s), a second subset of the plurality of videos. In some embodiments, the second subset may include, at least in part, the first subset or may be different videos from the first subset.

The method may further include using Hie first plurality of detections and frames from the second subset of the plurality of videos to train a generator network to generate a plurality of artificial representations of abnormalities. For example, the generator network may comprise a neural network configured to generate the artificial representations. In some embodiments, the generator network may comprise a convolutional neural network. The plurality of artificial representations may be generated through residual learning.

As explained above, training the generative network may include adjusting weights of one or more nodes of the network and/or adjusting activation (or transfer) functions of one or more nodes of the network. For example, as explained above, weights of the generative network may be adjusted to minimize a loss function associated with the network. Additionally or alternatively, activation (or transfer) functions of the generative network may be modified to improve the fit between one or more models of the node(s) and the input to the node(s).

The method may further include training, with the processor(s), an adversarial branch of the discriminator network to differentiate between the artificial representations of the abnormalities and true representations of abnormalities. For example, the adversarial branch may comprise a neural network that accepts representations as input and outputs indications of whether the input representation is artificial or true. In some embodiments, the neural network may comprise a convolutional neural network.

Similar to the generative branch, training the adversarial branch of the discriminator network may include adjusting weights of one or more nodes of the network and/or adjusting activation (or transfer) functions of one or more nodes of the network. For example, as explained above, weights of the adversarial branch of the discriminator network may be adjusted to minimize a loss function associated with the network. Additionally or alternatively, activation (or transfer) functions of the adversarial branch of the discriminator network may be modified to improve the fit between one or more models of the node(s) and the input to the node(s).

The method may further include applying, with the processor(s), the adversarial branch of the discriminator network to the plurality of artificial representations to produce difference indicators between the artificial representations of abnormalities and true representations of abnormalities included in frames of the second subset of plurality of videos. For example, the artificial representations may comprise representations of non-abnormalities that look similar to abnormalities. Accordingly, each artificial representation may provide a false representation of an abnormality that is highly similar to a true representation of an abnormality. The adversarial branch may learn to identify differences between non-abnormalities (the false representations) and abnormalities (the true representations), particularly non-abnormalities that are similar to abnormalities.

The method may further include applying, with the processor(s), the perception branch of the discriminator network to the artificial representations to produce a second plurality of detections of the abnormalities. Similar to the first plurality of detections, the second plurality of detections may comprise indicators of locations of abnormalities in the artificial representations, such as a point or a region of a detected abnormality. A lack of an abnormality may result in a null indicator or other indicator of no abnormality.

The method may further include retraining the perception branch based on the difference indicators and the second plurality of detections. For example, retraining the perception branch may include adjusting weights of one or more nodes of Hie network and/or adjusting activation (or transfer) functions of one or more nodes of the network. For example, as explained above, weights of the perception branch may be adjusted to minimize a loss function associated with the network. Additionally or alternatively, activation (or transfer) functions of the perception branch may be modified to improve the fit between one or more models of the node(s) and the difference indicators and the second plurality of detections.

The exemplary method of training described above may produce a trained neural network system. The trained neural network system may form part of a system used for detecting a feature-of-interest in images of a human organ (e.g., a neural network system may be implemented as part of overlay device 105 of FIG. 1). For example, such a system may include at least one memory configured to store instructions and at least one processor configured to execute the instructions. The at least one processor may select frames from a video of a human organ. For example, the video may comprise an endoscopy video.

The system processor(s) may apply a trained neural network system to the frames to produce at least one detection of the feature-of-interest. In some embodiments, the feature-of-interest may comprise an abnormality. The at least one detection may include an indicator of a location of the feature-of-interest. For example, the location may comprise a point of or a region including the detected feature-of-interest. The neural network system may have been trained to detect abnormalities as explained above.

In some embodiments, the system processor(s) may further apply one or more additional classifiers and/or neural networks to the detected feature-of-interest. For example, if the feature-of-interest comprises a lesion, the at least one processor may classify the lesion into one or more types (e.g., cancerous or non-cancerous, or the like). Additionally or alternatively, the neural network system may further output whether the detected feature-of-interest is a false positive or a true positive.

The system processor(s) may generate an indicator of a location of the at least one detection on one of the frames. For example, the location of the feature-of-interest may be extracted from the indicator and a graphic indicator of the location placed on the frame. In embodiments where the location comprises a point, the graphic indicator may comprise a circle, star, or any other shape placed on a point. In embodiments where the location comprises a region, the graphic indicator may comprise a border around the region. In some embodiments, the shape or border may be animated; accordingly, the shape or border may be generated for a plurality of frames such that it track the location of the feature-of-interest across the frames as well as appearing animated when the frames are shown in sequence. As explained further below, the graphic indicator may be paired with other indicators, such as a sound and/or a vibrational indicator.

Any aspect of the indicator may depend on a classification of the feature-of-interest, e.g., into one or more types or as a false or true positive. Accordingly, a color, shape, pattern, or other aspect of the graphical indicator may depend on the classification. In embodiments also using a sound and/or vibrational indicator, a duration, frequency, and/or amplitude of the sound and/or vibration may depend on the classification.

The system processor(s) may re-encode the frames into a video. Accordingly, after generating the (graphic) indicator and overlaying it on the frame(s), the frames may be re-assembled as a video. The processor(s) of the system may thus output the re-encoded video with the indicator.

According to another aspect of the present disclosure, a computer-implemented system (see, e.g., FIGS. 1 and 6) for processing real-time video is described. The system may comprise an input port for receiving real-time video. For example, the input port may comprise a video graphics array (VGA) port, a high-definition multimedia interface (HDMI) port, a digital visual interface (DVI) port, a Serial Digital Interface (SDI), or the like. The real-time video may comprise a medical video. For example, the system may receive the real-time video from an endoscopy device.

The system may further comprise a first bus for transferring the received real-time video. For example, the first bus may comprise a parallel connection or a serial connection and may be wired in a multidrop topology or a daisy chain topology. The first bus may comprise a PCI Express (Peripheral Component Interconnect Express) bus, a Universal Serial Bus (USB), an IEEE 1394 interface (FireWire), or the like.

The system may comprise at least one processor configured to receive the real-time video from the first bus, perform object detection on frames of the received real-time video, and overlay a border indicating a location of at least one detected object in the frames. The processor(s) may perform object detection using a neural network system trained to produce at least one detection of the object. In some embodiments, the at least one object may comprise a lesion or other abnormality. Accordingly, the neural network system may have been trained to detect abnormalities as explained above.

The processor(s) may overlay the border as explained above. For example, the border may surround a region including the object, the region being received with the at least one detection by the processor(s).

The system may further comprise a second bus for receiving the video with the overlaid border. For example, similar to the first bus, the second bus may comprise a parallel connection or a serial connection and may be wired in a multidrop topology or a daisy chain topology. Accordingly, like the first bus, the second bus may comprise a PCI Express (Peripheral Component Interconnect Express) bus, a Universal Serial Bus (USB), an IEEE 1394 interface (FireWire), or the like. The second bus may comprise the same type of bus as the first bus or may comprise a different type of bus.

The system may further comprise an output port for outputting the video with the overlaid border from the second bus to an external display. The output port may comprise a VGA port, an HDMI port, a DVI port, a SDI port, or the like. Accordingly, the output port may be the same type of port as the input port or may be a different type of port.

The system may comprise a third bus for directly transmitting the received real-time video to the output port. The third bus may carry the real-time video from the input port to the output port passively, to be effective even when the overall system is turned off. In some embodiments, the third bus may be the default bus that is active when the overall system is off. In such embodiments, the first and the second bus may be activated when the overall system is activated, and the third bus may be deactivated accordingly. The third bus may be re-activated when the overall system is turned off, or upon receipt of an error signal from the processor(s). For example, if the object detection implemented by the processor malfunctions, the processor(s) may activate the third bus, thereby allowing continued output of the real-time video stream without interruption due to the malfunction.

In some embodiments, the overlaid border may be modified across frames. For example, the overlaid border may comprise a two-dimensional shape that is displayed around a region of the image including the at least one detected object, the border being a first color. After an elapsed period of time, the processor(s) may modify the border to a second color if the at least one detected object is a true positive and to a third color if the at least one detected object is a false positive. Additionally or alternatively, the processor(s) may modify the border based on a classification of the detected object For example, if the object comprises a lesion or other abnormality, the modification may be based on whether the lesion or formation is cancerous or otherwise abnormal.

In any of the embodiments described above, the overlaid indicator may be paired with one or more additional indicators. For example, the processor(s) may transmit a command to one or more speakers to produce a sound when the at least one object is detected. In embodiments where the border is modified, the processor(s) may transmit the command when the border is modified. In such embodiments, at least one of duration, tone, frequency, and amplitude of the sound may depend on whether the at least one detected object is a true positive or a false positive. Additionally or alternatively, at least one of duration, tone, frequency, and amplitude of the sound may depend on a classification of the detected object.

Additionally or alternatively, the processor(s) may transmit a command to at least one wearable apparatus to vibrate when the at least one object is detected. In embodiments where the border is modified, the processor(s) may transmit the command when the border is modified. In such embodiments, at least one of duration, frequency, and amplitude of the vibration may depend on whether the at least one detected object is a true positive or a false positive. Additionally or alternatively, at least one of duration, tone, frequency, and amplitude of the vibration may depend on a classification of the detected object.

According to another aspect of the present disclosure, a system for processing real-time video is described. Similar to the processing system described above, the system may comprise an input port for receiving real-time video; at least one processor configured to receive the real-time video from the input port, perform object detection by applying a trained neural network on frames of the received real-time video, and overlay a border indicating a location of at least one detected object in the frames; and an output port for outputting the video with the overlaid border from the processor to an external display.

The system may further comprise an input device tor receiving a sensitivity setting from a user. For example, the input device may comprise a knob, one or more buttons, or any other device suitable for receiving one command to increase the setting and another command to decrease the setting.

The system processor(s) may adjust at least one parameter of the trained neural network in response to the sensitivity setting. For example, the processor(s) may adjust one or more weights of one or more nodes of the network to either increase or decrease the number of detections produced by the network, based on the sensitivity setting. Additionally or alternatively, one or more thresholds of the output layer of the network and/or applied to the detections received from the output layer of the network may be increased or decreased in response to the sensitivity setting. Accordingly, if the sensitivity setting is increased, the processor(s) may decrease the threshold(s) such that the number of detections produced by the network is increased. Similarly, if the sensitivity setting is decreased, the processor(s) may increase the threshold(s) such that the number of detections produced by the network is decreased.

FIG. 1 is a schematic representation of an exemplary system 100 including a pipeline for overlaying object detections on a video feed, consistent with embodiments of the present disclosure. As shown in the example of FIG. 1, system 100 includes an operator 101 who controls image device 103. In embodiments where the video feed comprises a medical video, operator 101 may comprise a physician or other health care professional. Image device 103 may comprise a medical imaging device, such as an X-ray machine, a computed tomography (CT) machine, a magnetic resonance imaging (MRI) machine, an endoscopy machine, or other medical imaging device that produces videos or one or more images of a human body or a portion thereof. Operator 101 may control image device 103 by controlling a capture rate of device 103 and/or a movement of device 103, e.g., through or relative to the human body. In some embodiments, image device 103 may comprise a Pill-Cam™ device or other form of capsule endoscopy device in lieu of an external imaging device, such as an X-ray machine, or an imaging device inserted through a cavity of the human body, such as an endoscopy device.

As further depicted in FIG. 1, image device 103 may transmit the captured video or images to an overlay device 105. Overlay device 105 may comprise one or more processors to process the video, as described above. Also, in some embodiments, operator 101 may control overlay 105 in addition to image device 103, for example, by controlling the sensitivity of an object detector (not shown) of overlay 105.

As depicted in FIG. 1, overlay device 105 may augment the video received from images device 103 and then transmit the augmented video to a display 107. In some embodiments, the augmentation may comprise the overlaying described above. As further depicted in FIG. 1, overlay device 105 may also be configured to relay the video from image device 103 directly to display 107. For example, overlay device 105 may perform a direct relay under predetermined conditions, such as if an object detector (not shown) included in overlay device 105 malfunctions. Additionally or alternatively, overlay device 105 may perform a direct relay if operator 101 inputs a command to overlay 105 to do so. The command may be received via one or more buttons included on overlay device 105 and/or through an input device such as a keyboard or the like.

Figure 2:
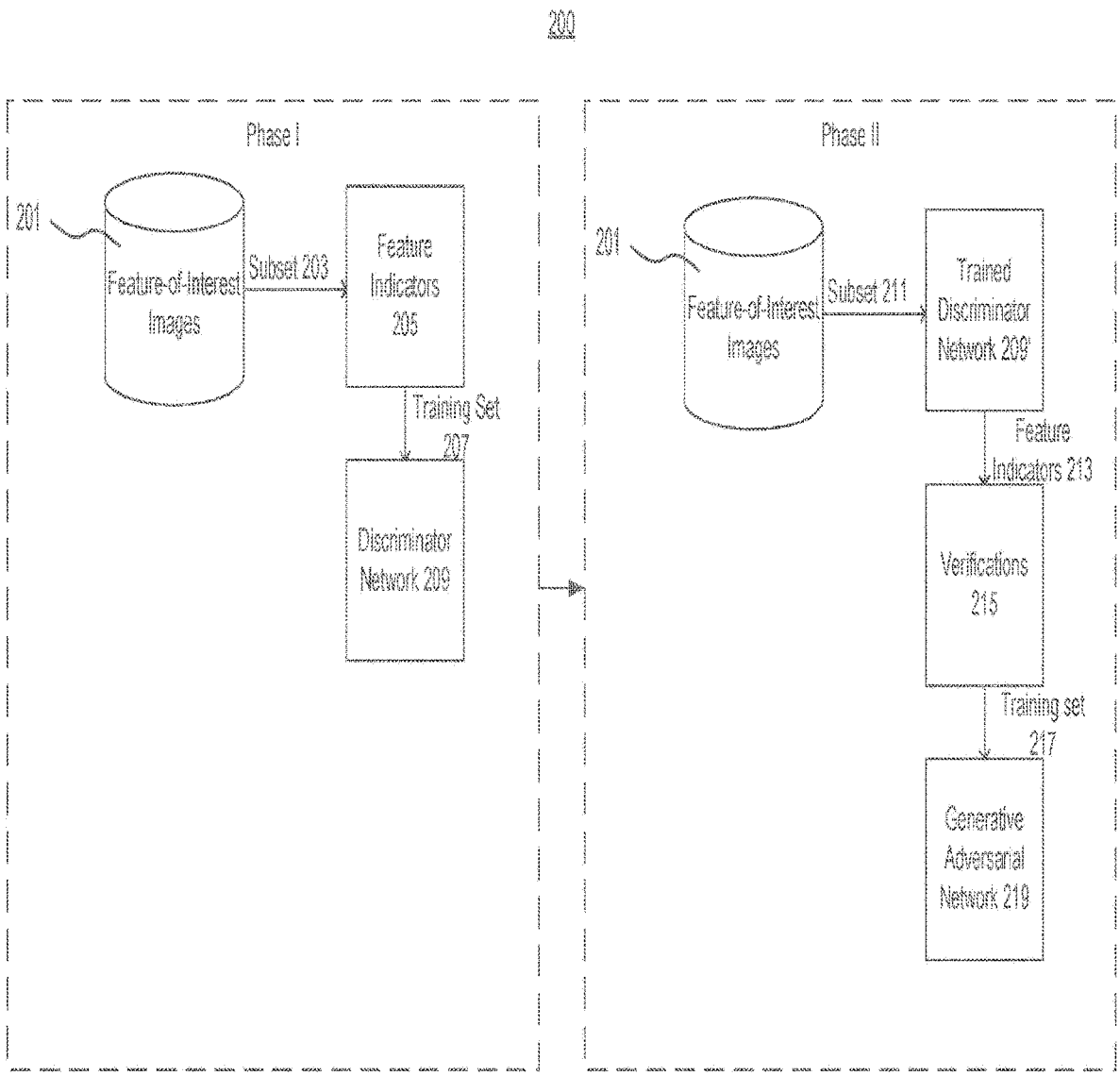
FIG. 2 is an exemplary two phase training loop for an object detection network, according to embodiments of the present disclosure.

FIG. 2 is a schematic representation of a two phase training loop 200 for an object detection network, consistent with embodiments of the present disclosure. Loop 200 may be implemented by one or more processors. As shown in FIG. 2, Phase I of loop 200 may use a database 201 of images including a feature-of-interest In embodiments where the images comprise medical images, the feature-of-interest may include an abnormality, such as a lesion.

As explained above, database 201 may store individual images and/or one or more videos, each video including a plurality of frames. During Phase I of loop 200, one or more processors may extract a subset 203 of images and/or frames from database 201. The one or more processors may select subset 203 randomly or, at least in part, using one or more patterns. For example, if database 201 stores videos, the one or more processors may select no more than one, two, or the like number of frames from each video included in subset 203.

As further depicted in FIG. 2, feature indicators 205 may comprise annotations to subset 203. For example, the annotations may include a point of or a region including the feature-of-interest. In some embodiments, an operator may view the video or images and manually input the annotations via an input device (e.g., any combination of a keyboard, mouse, touch screen, and display) to the processor(s). Annotations may be stored as in a data structure separate from the image, in formats such as JSON, XML, text, or the like. For example, in embodiments where the images are medical images, the operator may be a physician or other health care professional. Although depicted as added to subset 203 after extraction, subset 203 may have been annotated before storage in database 201 or at another earlier time. In such embodiments, the one or more processors may select subset 203 by selecting the images in database 201 having feature indicators 205.

Subset 203 together with feature indicators 205 comprise training set 207. The one or more processors may train a discriminator network 209 using training set 207. For example, discriminator network 209 may comprise an object detector network, as described above. As explained further above, training the discriminator network may include adjusting weights of one or more nodes of the network and/or adjusting activation (or transfer) functions of one or more nodes of the network. For example, weights of the object detection network may be adjusted to minimize a loss function associated with the network. In another example, activation (or transfer) functions of the object detection network may be modified to improve the fit between one or more models of the node(s) and the input to the node(s).

As shown in FIG. 2, during Phase 11 of loop 200, the one or more processors may extract a subset 211 of images (and/or frames) from database 201. Subset 211 may comprise, at least in part, some or all of the images from subset 203 or may comprise a different subset. In embodiments where subset 203 comprises a plurality of frames from one or more videos, subset 211 may include adjacent or other frames from one or more of the same videos. Subset 211 may comprise a larger number of images than subset 203, e.g., at least 100 times more images.

The one or more processors may apply discriminator network 209' (which represents the discriminator network 209 after the training of Phase I is completed) to subset 211 produce a plurality of feature indicators 213. For example, feature indicators 213 may comprise a point of or a region including a feature-of-interest detected by discriminator network 209'.

As further depicted in FIG. 2, verifications 215 may comprise annotations to feature indicators 213. For example, the annotations may include an indicator of whether each feature indicator is a true positive or a false positive. An image that had no feature-of-interest detected but includes the feature-of-interest may be annotated as a false negative.

Subset 211 together with feature indicators 2·13 and verifications 215 comprise training set 217. The one or more processors may train a generative adversarial network 219 using training set 217. For example, generative adversarial network 219 may comprise a generative network and an adversarial network, as described above. Training the generative adversarial network may include training the generative network to produce artificial representations of the feature-of-interest or of a false feature-of-interest that looks similar to a true feature-of-interest and training the adversarial network to distinguish the artificial representations from real representations, e.g., those included in subset 211.

Although not depicted in FIG. 2, verifications 2·13 may further be used to retrain discriminator network 209'. For example, weights and/or activation (or transfer) functions of discriminator network 209' may be adjusted to eliminate detections in images annotated as false positives and/or adjusted to produce detections in images annotated as false negatives.

Figure 3:
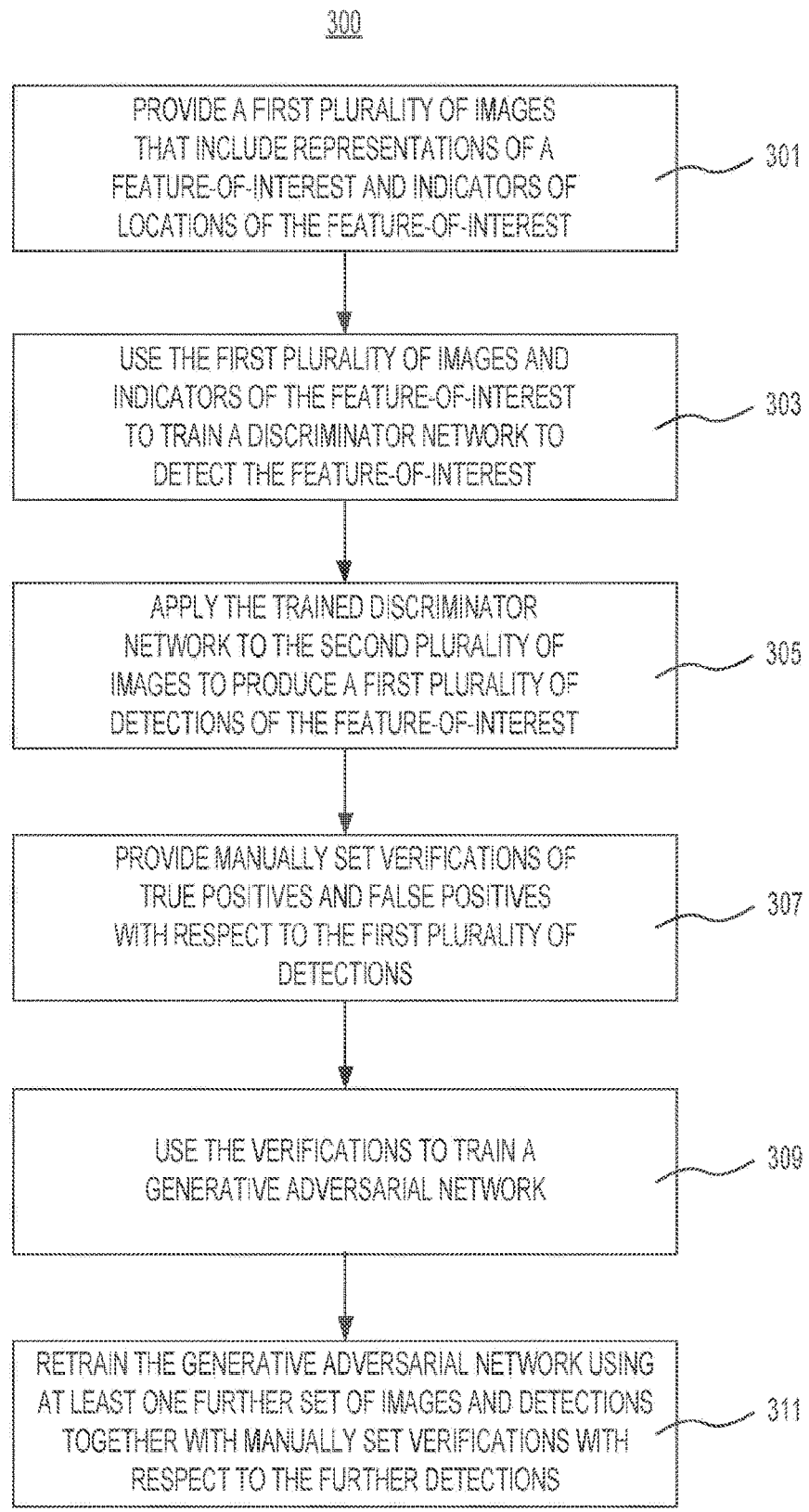
FIG. 3 is a flowchart of an exemplary method for training an object detection network, according to embodiments of the present disclosure.

FIG. 3 is a flowchart of an exemplary method 300 for training an object detection network. Method 300 may be performed by one or more processors. At step 301 in FIG. 3, at least one processor may provide a first plurality of images that include representations of the feature-of-interest and indicators of the locations of the feature-of-interest in images of the first plurality of images. The indicators may comprise manually set indicators. The manually set indicators may be extracted from a database or received as input from an operator.

At step 303, the at least one processor may, using the first plurality of images and indicators of the feature-of-interest, train an object detection network to detect the feature-of-interest. For example, the object detection network may be trained as explained above.

At step 305, the at least one processor may provide a second plurality of images that include representations of the feature-of-interest, the second plurality of images comprising a larger number of images than that included in the first plurality of images. In some embodiments, the second plurality of images may overlap, at least in part, with the first plurality of images. Alternatively, the second plurality of images may consist of different images than those in the first plurality.

At step 307, the at least one processor may apply the trained object detection network to the second plurality of images to produce a first plurality of detections of the feature-of-interest In some embodiments, as explained above, the detections may include indicators of locations of detected features-of-interest. For example, the object detection network may comprise a convolutional neural network outputting one or more matrices, each matrix defining coordinates and/or regions of any detected features-of-interest, optionally with one or more associated confidence scores for each detection.

At step 309, the at least one processor may provide manually set verifications of true positives and false positives with respect to the first plurality of detections. For example, the at least one processor may extract the manually set verifications from a database or receive them as input from an operator.

At step 311, the at least one processor may, using the verifications of the true positives and false positives with respect to the first plurality of detections, train a generative adversarial network. For example, the generative adversarial network may be trained as explained above.

At step 313, the at least one processor may retrain the generative adversarial network using at least one further set of images and detections of the feature-of-interest, together with further manually set verifications of true positives and false positives with respect to the further detections of the feature-of-interest. In some embodiments, the further set of images may overlap, at least in part, with the first plurality of images and/or the second plurality of images. Alternatively, the further set of images may consist of different images than those in the first plurality and those in the second plurality. Step 313 may thus comprise applying the trained object detection network to the further set of images to produce further detections of the feature-of-interest, providing manually set verifications of true positives and false positives with respect to the further detections, and retraining the generative adversarial network using the verifications with respect to the further detections.

Consistent with the present disclosure, the example method 300 may include additional steps. For example, in some embodiments, method 300 may include retraining the generative adversarial network by providing verifications of false negatives for missed detections of the feature-of-interest in two or more images. Accordingly, the manually set verifications extracted from a database or received as input, may include verifications of false negatives as well as verifications of true positives and false positives. The false negatives may be used to retrain the generative adversarial network. Additionally or alternatively, the false negatives may be used to retrain the object detection network.

Figure 4:
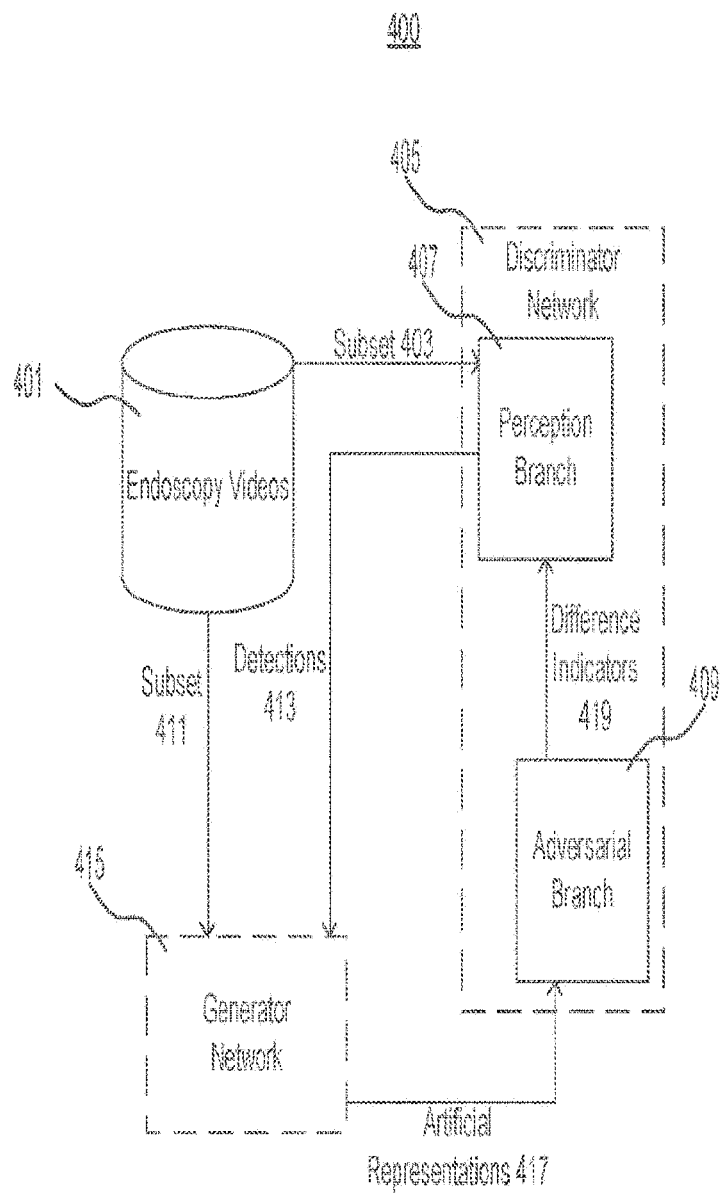
FIG. 4 is a schematic representation of an exemplary object detector with a discriminator network and a generative network, according to embodiments of the present disclosure.

FIG. 4 is a schematic representation of an object detector 400. Object detector 400 may be implemented by one or more processors. As shown in FIG. 4, object detector 400 may use a database 401 of videos including a feature-of-interest. In embodiments where the images comprise medical image, the feature-of-interest may include an abnormality, such as a lesion. In the example of FIG. 4, database 401 comprises a database of endoscopy videos.

As further depicted in FIG. 4, detector 400 may extract a subset 403 of videos from database 401. As explained above with respect to FIG. 2, subset 403 may be selected randomly and/or using one or more patterns. Detector 400 may apply a perception branch 407 of a discriminator network 405 to frames of subset 403. Perception branch 407 may comprise an object detection network, as described above. Perception branch 407 may have been trained to detect the feature-of-interest and identify a location (e.g., a point or a region) associated with a detected feature-of-interest. For example, perception branch 407 may detect abnormalities and output bounding boxes including the detected abnormalities.

As shown in FIG. 4, perception branch 407 may output detections 413. As explained above, detections 413 may include points or regions identifying locations of detected features-of-interest in subset 403. As further depicted in FIG. 4, detector 400 may extract a subset 411 of videos from database 401. For example, subset 411 may overlay, at least in part, with subset 403 or consist of different videos. Subset 411 may have a larger number of videos than subset 403, e.g., at least 100 times more videos. Detector 400 may use subset 411 and detections 413 to train a generative network 415. Generative network 415 may be trained to produce artificial representations 417 of the feature-of-interest, e.g., abnormalities. Artificial representations 417 may comprise false representations of the feature-of-interest that look similar to true representations of the feature-of-interest. Accordingly, generative network 415 may be trained to fool perception branch 407 into making detections that are false positives.

As further depicted in FIG. 4, generative network 415, once trained, may produce artificial representations 417. Detector 400 may use artificial representations 417 to train an adversarial branch 409 of discriminator network 405. As described above, adversarial branch 409 may be trained to distinguish artificial representations 417 from subset 411. Accordingly, adversarial branch 409 may determine difference indicators 419. Difference indicators 419 may represent any feature vectors or other aspects of an image that are present in artificial representations 4·17 but not in subset 411, present in subset 411 but not in artificial representations 417, or subtractive vectors or other aspects representing differences between feature vectors or other aspects of artificial representations 417 and those of subset 411.

As depicted in FIG. 4, detector 400 may retrain perception branch 407 using difference indicators 419. For example, in embodiments where artificial representations 4·17 comprise false representations of the feature-of-interest, detector 400 may retrain perception branch 407 such that the false representations do not result in detections true representation in subset 411.

Although not depicted in FIG. 4, detector 400 may further use recursive training to improve generative network 415, perception branch 407, and/or adversarial branch 409.

For example, detector 400 may retrain generator network 415 using difference indicators 419. Accordingly, the output of adversarial branch 409 may be used to retrain generator network 415 such that the artificial representations look even more similar to true representations. Additionally, retrained generator network 415 may produce a new set of artificial representations used to retrain adversarial branch 409. Accordingly, adversarial branch 409 and generator network 415 may engage in unsupervised learning, the output of each being used to retrain the other in a recursive manner. This recursive training may be repeated until a threshold number of cycles has been reached and/or until a loss function associated with generator network 415 and/or a loss function associated with adversarial branch 409 reaches a threshold. Moreover, during this recursive training, perception branch 407 may also be retrained using each new output of difference indicators, such that a new subset with new detections may be used to further retrain generator network 415.

Figure 5:
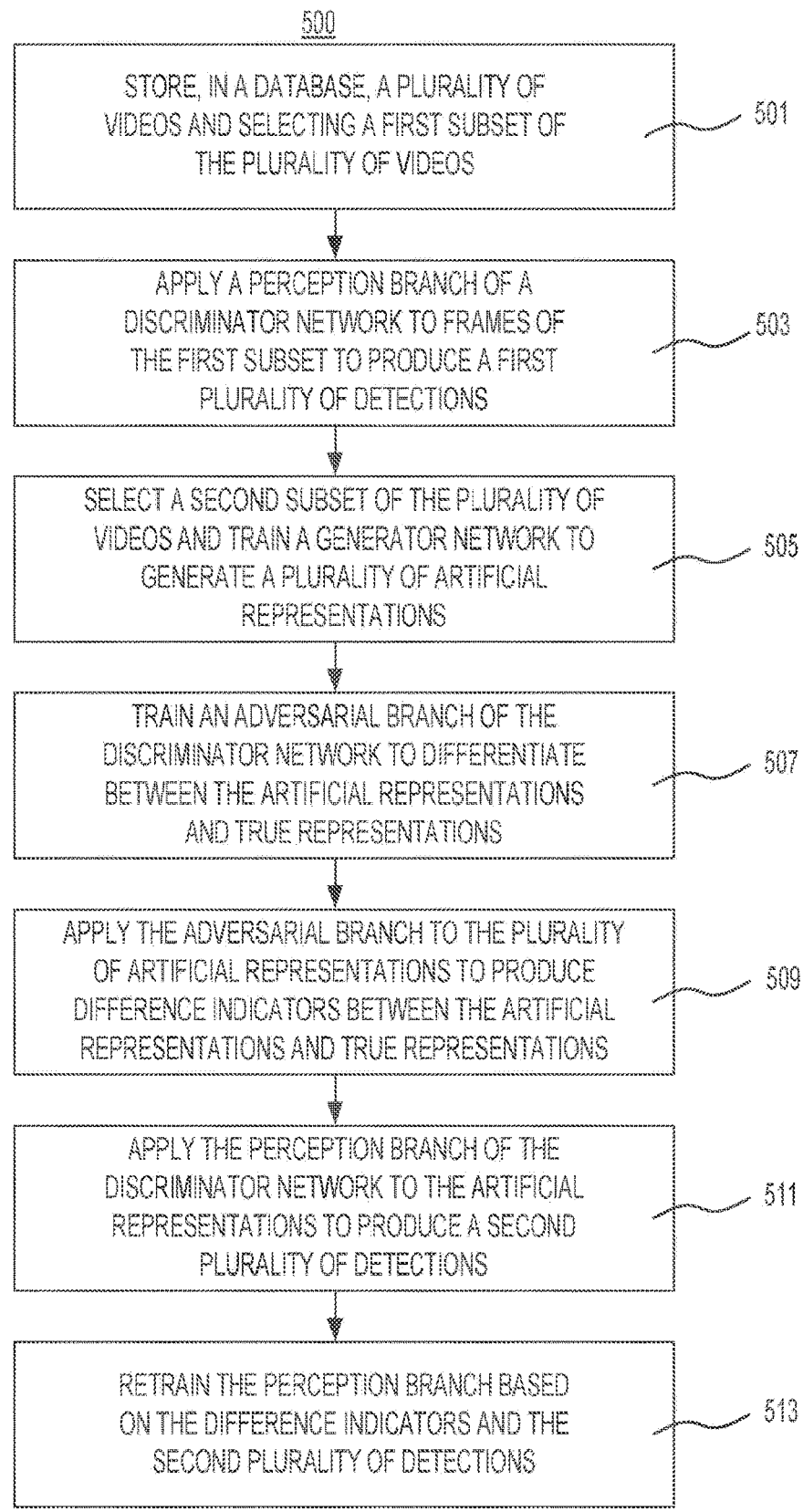
FIG. 5 is a flowchart of an exemplary method for detecting a feature-of-interest using a discriminator network and a generator network, according to embodiments of the present disclosure.

FIG. 5 is a flowchart of an exemplary method 500 for detecting a feature-of-interest using a discriminator network and a generator network. Method 500 may be performed by one or more processors.

At step 501 in FIG. 5, at least one processor may store, in a database, a plurality of videos including representations of a feature-of-interest, such as abnormalities. For example, the videos may have been captured during endoscopy procedures. As part of step 501, the at least one processor may further select a first subset of the plurality of videos. As explained above, the at least one processor may select randomly and/or using one or more patterns.

At step 503, the at least one processor may apply a perception branch of an object detection network to frames of the first subset of the plurality of videos to produce a first plurality of detections of abnormalities. In some embodiments, as explained above, the detections may include indicators of locations of detected abnormalities. Also, in some embodiments the perception branch may comprise a convolutional neural network, as explained above.

At step 505, the at least one processor may select a second subset of the plurality of videos. As explained above, the at least one processor may select randomly and/or using one or more patterns. Using the first plurality of detections and frames from the second subset of the plurality of videos, the at least one processor may further train a generator network to generate a plurality of artificial representations of abnormalities, the plurality of artificial representations being generated through residual learning. As explained above, each artificial representation provides a false representation of an abnormality that is highly similar to a true representation of an abnormality.

At step 507, the at least one processor may train an adversarial branch of the discriminator network to differentiate between the artificial representations of the abnormalities and true representations of abnormalities. For example, as explained above, the adversarial branch may be trained to identify differences between the artificial representations and the true representations in the frames. In some embodiments, the adversarial branch may comprise a convolutional neural network, as explained above.

At step 509, the at least one processor may apply the adversarial branch of the discriminator network to Hie plurality of artificial representations to produce difference indicators between the artificial representations of abnormalities and true representations of abnormalities included in frames of the second subset of plurality of videos. For example, as explained above, the difference indicators may represent any feature vectors or other aspects of an image that are present in the artificial representations but not in the frames, are present in the frames but not in the artificial representations, or are subtractive vectors or other aspects representing differences between feature vectors or other aspects of the artificial representations and those of the frames.

At step 511, the at least one processor may apply the perception branch of the discriminator network to the artificial representations to produce a second plurality of detections of the abnormalities. Similar to the first plurality of detections, the detections may include indicators of locations of detected abnormalities in the artificial representations.

At step 513, the at least one processor may retrain the perception branch based on the difference indicators and the second plurality of detections. For example, in embodiments where each artificial representation provides a false representation of an abnormality that is highly similar to a true representation of an abnormality, the at least one processor may retrain the perception branch to decrease the number of detections returned from the artificial representations and, accordingly, to increase the number of null indicators or other indicators of no abnormality returned from the artificial representations.

Consistent with the present disclosure, the example method 500 may include additional steps. For example, in some embodiments, method 500 may include retraining the generative network based on the difference indicators. In such embodiments, method 500 may further include applying the generative network to generate a further plurality of artificial representations of abnormalities and retraining the adversarial branch based on the further plurality of artificial representations of abnormalities. Such retraining steps may be recursive. For example, method 500 may include applying the retrained adversarial branch to the further plurality of artificial representations to produce further difference indicators between the further artificial representations of abnormalities and true representations of abnormalities included in frames of the second subset of plurality of videos and retraining the generative network based on the further difference indicators. As explained above, this recursive retraining may be repeated until a threshold number of cycles has been reached and/or until a loss function associated with the generative network and/or a loss function associated with the adversarial branch reaches a threshold.

FIG. 6 is a schematic representation of a system 600 comprising a hardware configuration for a video feed, consistent with embodiments of the present disclosure. As shown in FIG. 6, system 600 may be communicably coupled to an image device 601, such as a camera or other device outputting a video feed. For example, image device 601 may comprise a medical imaging device, such as CT scanner, an MRI machine, an endoscopy device, or the like. System 600 may further be communicably coupled to a display 615 or other device for displaying or storing video. For example, display 615 may comprise a monitor, screen, or other device for displaying images to a user. In some embodiments, display 615 may be replaced with or supplemented by a storage device (not shown) or a network interface controller (NIC) communicably connected to a cloud-based storage system (also not shown).

As further depicted in FIG. 6, system 600 may include an input port 603 for receiving the video feed from camera 601, as well as an output port 611 for outputting video to display 615. As explained above, input port 603 and output port 611 may comprise VGA ports, HDMI ports, DVI ports, or the like.

System 600 further includes a first bus 605 and a second bus 613. As shown in FIG. 6, first bus 605 may transmit video received through input port 603 through at least one processor 607. For example, processor(s) 607 may implement any of the object detector networks and/or discriminator networks described above. Accordingly, processor(s) 607 may overlay one or more indicators, e.g., the exemplary graphical indicator of FIG. 8, on the video received via first bus 602, e.g., by using the exemplary method 700 of FIG. 7. Processor 607 may then transmit the overlaid video via a third bus 609 to output port 611.

In certain circumstances, the object detector implemented by processor(s) 607 may malfunction. For example, the software implementing the object detector may crash or otherwise stop functioning properly. Additionally or alternatively, processor(s) 607 may receive a command to halt overlaying the video (e.g., from an operator of system 600). In response to the malfunction and/or the command, processor(s) 607 may activate second bus 613. For example, processor(s) 607 may send a command or other signal, as depicted in FIG. 6, to activate second bus 613.

As depicted in FIG. 6, second bus 6·13 may transmit received video directly from input port 603 to output port 611, thereby allowing system 600 to function as a pass-through for image device 601. Second bus 613 may allow for seamless presentation of video from image device 601 even if software implemented by processor 607 malfunctions or if an operator of hardware overlay 600 decides to halt the overlaying in Hie middle of the video feed.

Figure 7:
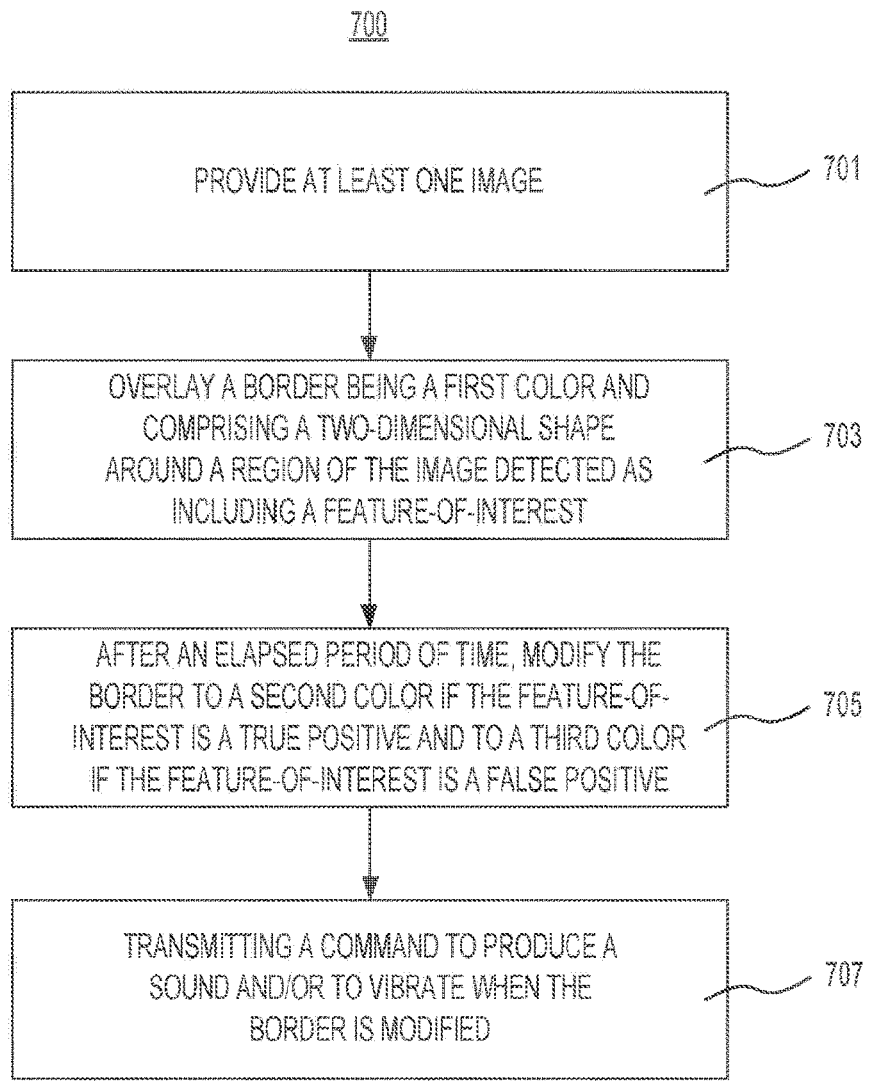
FIG. 7 is a flowchart of an exemplary method for overlaying object indicators on a video feed using an object detector network, according to embodiments of the present disclosure.

FIG. 7 is a flowchart of an exemplary method 700 for overlaying object indicators on a video feed using an object detector network, consistent with embodiments of the present disclosure. Method 700 may be performed by one or more processors. At step 701 in FIG. 7, at least one processor may provide at least one image. For example, the at least one image may be extracted from a database or received from an imaging device. In some embodiments, the at least one image may comprise a frame within the video feed.

At step 703, the at least one processor may overlay a border comprising a two-dimensional shape around a region of the image detected as including the feature-of-interest, the border being rendered in a first color. At step 705, after an elapsed period of time, the at least one processor may modify the border to appear in a second color if the feature-of-interest is a true positive, and to appear in a third color if the feature-of-interest is a false positive. The elapsed period of time may represent a preset period (e.g., a threshold number of frames and/or seconds) and/or may represent an elapsed time between detection of the feature-of-interest and classification thereof as a true or false positive.

Additionally or alternatively, the at least one processor may modify the border to the second color if the feature-of-interest is classified in a first category, and modify the border to the third color if the feature-of-interest is classified in a second category. For example, if the feature-of-interest is a lesion, the first category may comprise cancerous lesions and the second category may comprise non-cancerous lesions.

Consistent with the present disclosure, the example method 700 may include additional steps. For example, in some embodiments, method 700 may include transmitting a command to one or more speakers to produce a sound when the border is modified and/or transmitting a command to at least one wearable apparatus to vibrate when the border is modified. In such embodiments, at least one of duration, tone, frequency, and amplitude of the sound and/or the vibration may depend on whether the at least one detected object is a true positive or a false positive.

Figure 8A:
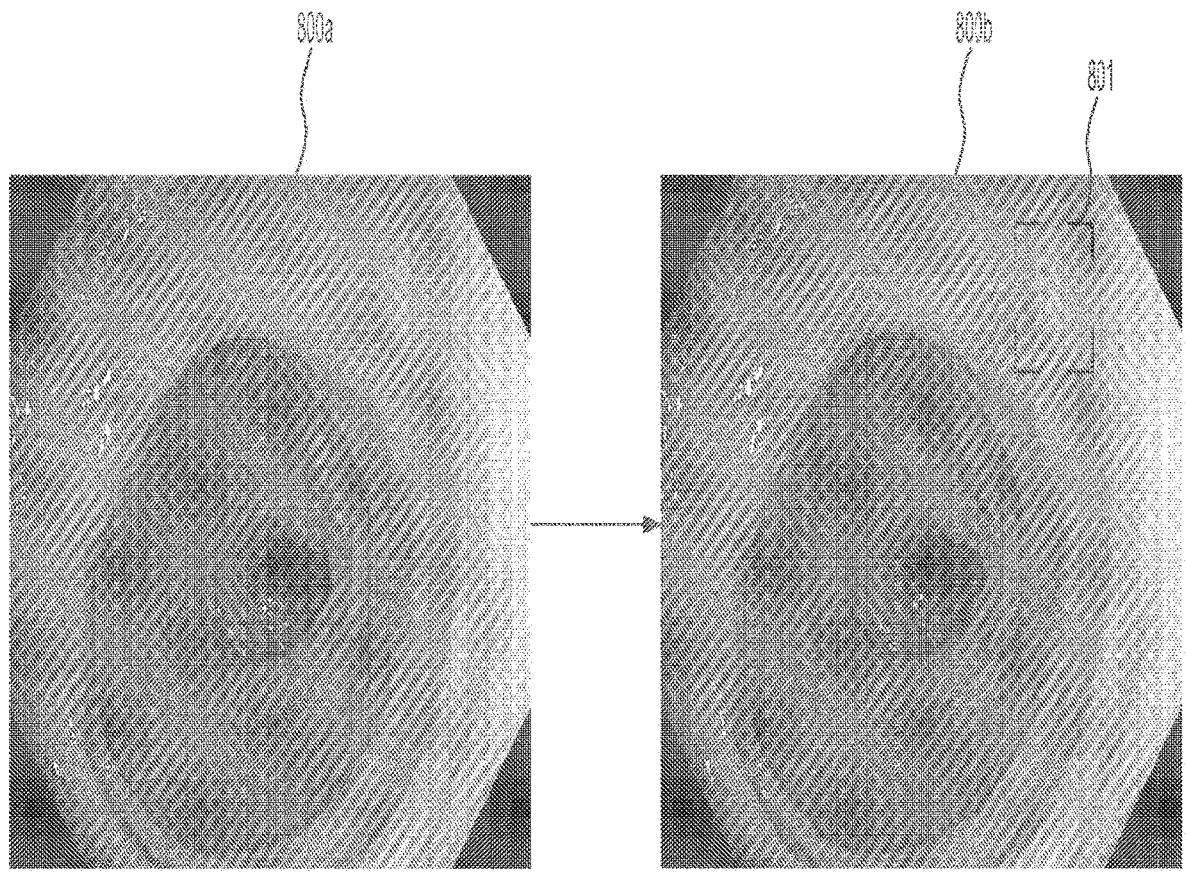
FIG. 8A is an example of a display with an overlay for object detection in a video, according to embodiments of the present disclosure.

FIG. 8A illustrates an example overlay 801 for object detection in a video, consistent with embodiments of the present disclosure. In the example of FIG. 8A, as well as FIGS. 8B and 8C, the illustrated video samples 800a and 800b are from a colonoscopy procedure. It will be appreciated from the present disclosure, video from other procedures and imaging devices may be utilized when implementing embodiments of the present disclosure. Thus, the video samples 800a and 800b are non-limiting examples of the present disclosure. In addition, by way of example, the video display of FIGS. 8A-8C may be presented on a display device, such as display 107 of FIG. 1 or display 615 of FIG. 6.

Overlay 801 represents one example of a graphical border used as an indicator for a detected abnormality or feature-of-interest in a video. As shown in FIG. 8A, images 800a and 800b comprise frames of a video including a detected feature-of-interest. Image 800b includes graphical overlay 801 and corresponds to a frame that is further in sequence, or later in time, than image 800a.

As shown in FIG. 8A, images 800a and 800b comprise video frames from a colonoscopy, and the feature-of-interest comprises a lesion or polyp. In other embodiments, as described above, images from other medical procedures, such as gastroscopy, enteroscopy, or the like, may be utilized and overlaid with a graphical indicator, such as overlay 801. In some embodiments, indicator 801 may be overlaid after detection of the abnormality and an elapse of time (e.g., a particular number of frames and/or seconds between image 800a and image 800b). In the example of FIG. 8A, overlay 801 comprises an indicator in the form of rectangular border with a predetermined pattern (i.e., solid corner angles). In other embodiments, overlay 801 may be a different shape (whether regular or irregular). In addition, overlay 801 may be displayed in a predetermined color, or transition from a first color to another color.

In the example of FIG. 8A, overlay 801 comprises an indicator with solid corner angles surrounding the detected location of the feature-of-interest in the video frame. Overlay 801 appears in video frame 800b, which may follow in sequence from video frame 800a.

Figure 8B:
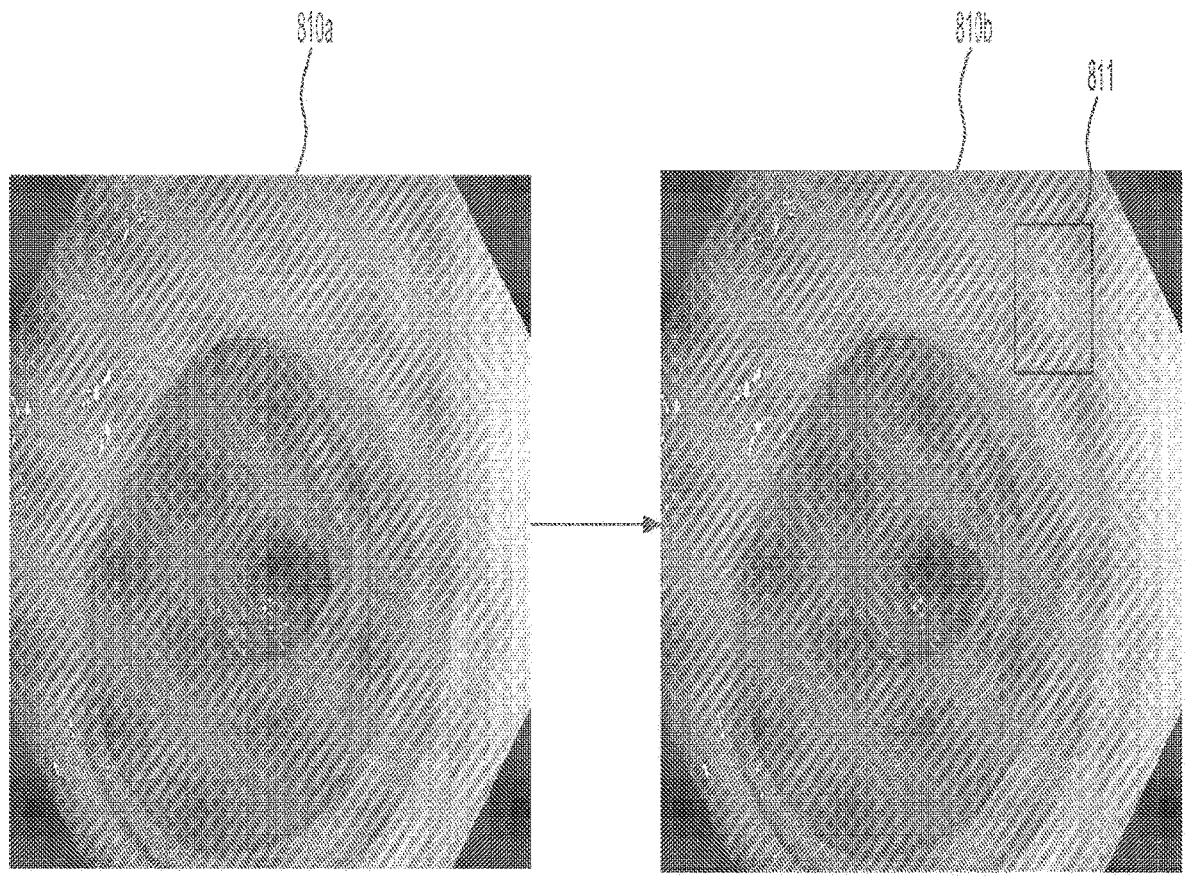
FIG. 8B is another example of a display with an overlay for object detection in a video, according to embodiments of the present disclosure.

FIG. 8B illustrates another example of a display with an overlay for object detection in a video, according to embodiments of the present disclosure. FIG. 88 depicts an image 810a (similar to image 800a) and a later image 810b (similar to image 800b) that is overlaid with an indicator 811. In the example of FIG. 8B, overlay 811 comprises a rectangular border with sold lines on all sides. In other embodiments, overlay 811 may be a first color and/or a different shape (whether regular or irregular). In addition, overlay 811 may be displayed in a predetermined color, or transition from a first color to another color. As shown in FIG. 8B, overlay 811 is placed over the detected abnormality or feature-of-interest in the video. Overlay 811 appears in video frame 810b, which may follow in sequence from video frame 810a.

Figure 8C:
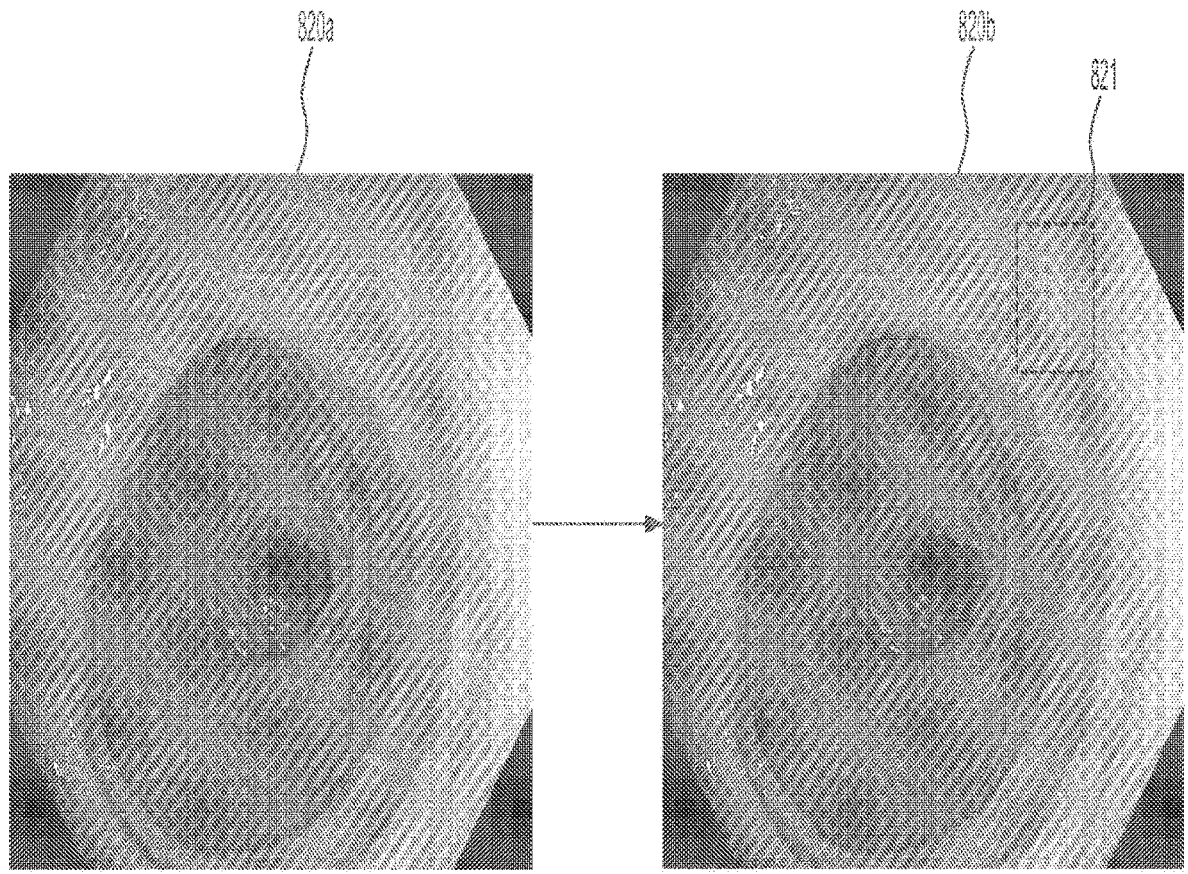
FIG. 8C is an example of a display with an overlay tor object detection in a video, according to embodiments of the present disclosure.

FIG. 8C illustrates another example of a display with an overlay for object detection in a video, according to embodiments of the present disclosure. FIG. BC depicts an image 820a (similar to image 800a) and a later image 820b (similar to image 800b) that is overlaid with an indicator 821. In the example of FIG. 8C, overlay 821 comprises a rectangular border with dashed lines on all sides. In other embodiments, indicator 821 may be a different shape (whether regular or irregular). In addition, overlay 821 may be displayed in a predetermined color, or transition from a first color to another color. As shown in FIG. 8C, overlay 821 is placed over the detected abnormality or feature-of-interest in the video. Overlay 821 appears in video frame 820b, which may follow in sequence from video frame 820a.

In some embodiments, the graphical indicator (i.e., overlay 801, 811, or 821) may change pattern and/or color. For example, the pattern and/or color of the border of the pattern may be modify in response to an elapse of time (e.g., a particular number of frames and/or seconds between image 800a and image 800b, image 810a and image 810b, or image 820a and image 820b). Additionally, or alternatively, the pattern and/or color of the indicator may be modified in response to a particular classification of the feature-of-interest (e.g., if the feature-of-interest is a polyp, a classification of the polyp as cancerous or non-cancerous, etc.). Moreover, the pattern and/or color of the indicator may depend on the classification of the feature-of-interest. Accordingly, the indicator may have a first pattern or color if the feature-of-interest is classified in a first category, a second pattern or color if the feature-of-interest is classified in a second category, etc. Alternatively, the pattern and/or color of the indicator may depend on whether the feature-of-interest is identified as a true positive or a false positive. For example, the feature-of-interest may be detected by an object detector network (or a perception branch of a discriminator network), as described above, resulting in the indicator, but then determined to be a false positive by an adversarial branch or network, as described above, resulting in the indicator being a first pattern or color. The indicator may be displayed in a second pattern or color if, instead, the feature-of-interest is determined to be a true positive by the adversarial branch or network.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware, but systems and methods consistent with the present disclosure can be implemented with hardware and software. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A computer-implemented system for detecting a feature-of-interest in at least one of a video and an image, the system comprising:
   a generative network configured to generate artificial representations of the feature-of-interest based on detections of the feature-of-interest, the artificial representations including false representations that appear as true representations of the feature-of-interest; and
   a discriminator network configured to be trained based on the artificial representations of the feature-of-interest to provide an output identifying differences between the false representations and true representations of the feature-of-interest, and wherein the discriminator network is further configured to be trained based on the output such that false representations are not detected by the discriminator network as true representations.

2. The system of claim 1, wherein the generative network is further configured to generate the artificial representations based on a set of at least one of videos and images that include the feature-of-interest and that are stored in a database.

3. The system of claim 2, wherein the output of the discriminator network comprises feature vectors indicating features that are present in the artificial representations but not in the feature-of-interest included in the set.

4. The system of claim 1, wherein the generative network is further configured to be trained by the output such that the artificial representations include true representations.

5. The system of claim 1, wherein the feature-of-interest comprises at least one of a formation on or of human tissue, a change in human tissue from one type of cell to another type of cell, an absence of human tissue from a location where human tissue is expected, or a lesion.

6. The system of claim 1, wherein the discriminator network comprises a convolutional neural network.

7. The system of claim 1, wherein the feature-of-interest comprises an abnormality on or of human tissue.

8. The system of claim 1, wherein the feature-of-interest comprises an object.

9. A computer-implemented method for detecting a feature-of-interest in at least one of a video and an image, the method comprising the following steps performed by at least one processor:
   generating, based on detections of the feature-of-interest, artificial representations of the feature-of interest, the artificial representations including false representations that appear as true representations of the feature-of-interest;
   training a network, based on the artificial representations, to provide an output identifying differences between the false representations and true representations of the feature-of-interest; and
   further training the network, based on the output, such that false representations are not detected by the network as true representations.

10. The method of claim 9,
    wherein generating the artificial representations includes generating the artificial representations based on a set of at least one of videos and images, from a database, that include the feature-of-interest.

11. The method of claim 10, wherein the output comprises feature vectors indicating features that are present in the artificial representations but not in the feature-of-interest included in the set.

12. The method of claim 9, wherein the feature-of-interest comprises at least one of a formation on or of human tissue, a change in human tissue from one type of cell to another type of cell, an absence of human tissue from a location where human tissue is expected, or a lesion.

13. The method of claim 9, wherein the network comprises a convolutional neural network.

14. The method of claim 9, wherein the feature-of-interest comprises an abnormality on or of human tissue.

15. The method of claim 9, wherein the feature-of-interest comprises an object.

* * * * *